United States Patent
Aird et al.

(10) Patent No.: US 11,524,009 B2
(45) Date of Patent: Dec. 13, 2022

(54) COMBINATION COMPRISING AT LEAST ONE SPLICEOSOME MODULATOR AND AT LEAST ONE INHIBITOR CHOSEN FROM BCL2 INHIBITORS, BCL2/BCLXL INHIBITORS, AND BCLXL INHIBITORS AND METHODS OF USE

(71) Applicant: Eisai R&D Management Co., Ltd., Tokyo (JP)

(72) Inventors: Daniel Aird, Reading, MA (US); Laura Corson, Brookline, MA (US); Ping Zhu, Boxboro, MA (US); Markus Warmuth, Newton, MA (US); Silvia Buonamici, Boston, MA (US); Peter Gerard Smith, Arlington, MA (US); Peter Fekkes, Waltham, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 16/760,313

(22) PCT Filed: Oct. 30, 2018

(86) PCT No.: PCT/US2018/058277
§ 371 (c)(1),
(2) Date: Apr. 29, 2020

(87) PCT Pub. No.: WO2019/089641
PCT Pub. Date: May 9, 2019

(65) Prior Publication Data
US 2020/0352937 A1 Nov. 12, 2020

Related U.S. Application Data

(60) Provisional application No. 62/579,666, filed on Oct. 31, 2017, provisional application No. 62/580,364, filed on Nov. 1, 2017.

(51) Int. Cl.
| | | |
|---|---|---|
| A61K 31/496 | (2006.01) | |
| A61P 35/00 | (2006.01) | |
| A61K 31/05 | (2006.01) | |
| A61K 31/11 | (2006.01) | |
| A61K 31/166 | (2006.01) | |
| A61K 31/343 | (2006.01) | |
| A61K 31/352 | (2006.01) | |
| A61K 31/395 | (2006.01) | |
| A61K 31/404 | (2006.01) | |
| A61K 31/426 | (2006.01) | |
| A61K 31/4355 | (2006.01) | |
| A61K 31/4725 | (2006.01) | |
| A61K 31/495 | (2006.01) | |
| A61K 31/5355 | (2006.01) | |

(52) U.S. Cl.
CPC .......... *A61K 31/496* (2013.01); *A61K 31/05* (2013.01); *A61K 31/11* (2013.01); *A61K 31/166* (2013.01); *A61K 31/343* (2013.01); *A61K 31/352* (2013.01); *A61K 31/395* (2013.01); *A61K 31/404* (2013.01); *A61K 31/426* (2013.01); *A61K 31/4355* (2013.01); *A61K 31/4725* (2013.01); *A61K 31/495* (2013.01); *A61K 31/5355* (2013.01); *A61P 35/00* (2018.01)

(58) Field of Classification Search
CPC .................................................... A61K 31/496
USPC ..................................................... 514/235.8
See application file for complete search history.

(56) References Cited

U.S. PATENT DOCUMENTS

| | | | |
|---|---|---|---|
| 8,048,888 B2* | 11/2011 | Wosikowski-Buters | A61K 31/555 514/266.4 |
| 8,455,477 B2* | 6/2013 | Katz | A61P 3/10 514/210.18 |
| 9,682,993 B2* | 6/2017 | Webb | C07D 493/10 |
| 2015/0313906 A1* | 11/2015 | Creasy | A61K 31/35 514/235.5 |
| 2016/0009728 A1 | 1/2016 | Webb et al. | |

FOREIGN PATENT DOCUMENTS

| | | |
|---|---|---|
| CN | 106211774 A | 12/2016 |
| WO | WO 2010/138488 A1 | 12/2010 |
| WO | WO 2014/089571 A1 | 6/2014 |
| WO | WO 2014/100080 A1 | 6/2014 |
| WO | WO 2015/015401 A2 | 2/2015 |

OTHER PUBLICATIONS

Larrayoz, Leukemia, 2015, 30(27), 357-359.*
Larroyoz, Leukemia 30(27), 351-360, 2015.*
International Search Report and Written Opinion for PCT/JP2018/058277 dated Mar. 6, 2019 2018 (6 pages).
Larrayoz, M. et al., "The SF3B1 Inhibitor Spliceostatin A (SSA) Elicits Apoptosis in Chronic Lymphocytic Leukaemia Cells Through Downregulation of Mcl-I.", Leukemia, vol. 30, Nov. 27, 2015, pp. 351-360.
Buonamici, S. et al., Abstract 1185: H3B-8800, a Novel Orally Available SF3b Modulator, shows Preclinical Efficacy Across Spliceosome Mutant Cancers, Exp Mol Ther, Jul. 31, 2017, vol. 77, No. 13, (2 pages).

(Continued)

*Primary Examiner* — Nizal S Chandrakumar
(74) *Attorney, Agent, or Firm* — Finnegan, Henderson, Farabow, Garrett & Dunner, LLP

(57) ABSTRACT

The present disclosure provides pharmaceutical combinations comprising at least one spliceosome modulator and at least one inhibitor chosen from BCL2, BCL2/BCLxL, and BCLxL inhibitors. Also provided are methods of treating cancer comprising administering a therapeutically effective amount of at least one spliceosome modulator and a therapeutically effective amount of at least one inhibitor chosen from BCL2, BCL2/BCLxL, and BCLxL inhibitors.

34 Claims, 24 Drawing Sheets

Specification includes a Sequence Listing.

(56) References Cited

OTHER PUBLICATIONS

Gao, Yang et al., "Regulation of HPV16 E6 and MCL1 by SF3B1 Inhibitor in Head and Neck Cancer Cells," Sci Rep, Aug. 20, 2014, vol. 4, p. 6098 (pp. 1-10).

Laetsch, T.W. et al., Multiple Components of the Spliceosome Regulate McL1 Activity in Neuroblastoma, Cell DeatDis, Feb. 20, 2014, vol. 5, No. 2, p. e1072 (pp. 1-12).

Salton M. et al., "Small Molecule Modulators of Pre-mRNA Splicing in Cancer Therapy," Trends Mol Med, Dec. 14, 2015, vol. 22, No. 1, pp. 28-37.

Ten Hacken, E. et al., "Splicing Modulation Perturbs Key Survival Pathways and Sensitizes Chronic Lymphocytic Leukemia to Venetoclax Treatment," Blood, Dec. 8, 2017, vol. 130, No. Suppl 1, p. 264.

Yoshimi, Akihide et al., "Molecular Pathways: Understanding and Targeting Mutant Spliceosomal Proteins," Clin. Cancer Res. Jan. 2017, vol. 23, N.2, pp. 336-341.

Search Report from Intellectual Property Office of Singapore for corresponding SG 11202003197T dated Sep. 30, 2021 (3 pages).

Search Report from Russian Patent Office for corresponding RU 2020117201 dated Mar. 29, 2022 (3 pages).

\* cited by examiner

LOEWE MODEL

LOEWE EXCESS | JJN3.1

GROWTH INHIBITION (%) N=1

| H3B-8800 (µM) \ VENETOCLAX (ABT-199) (µM) | 0 | 3.5e-5 | 8e-4 | .0069 | .0060 | .061 | .55 | 5 |
|---|---|---|---|---|---|---|---|---|
| 5 | 183 | 183 | 183 | 183 | 183 | 183 | 183 | 183 |
| .55 | 178 | 178 | 178 | 178 | 178 | 178 | 178 | 178 |
| .061 | 167 | 167 | 167 | 167 | 167 | 167 | 167 | 167 |
| .0069 | 146 | 146 | 146 | 146 | 146 | 146 | 146 | 146 |
| .0060 | 115 | 115 | 115 | 115 | 115 | 115 | 115 | 115 |
| 8e-4 | 80 | 80 | 80 | 80 | 80 | 80 | 80 | 80 |
| 3.5e-5 | 46 | 46 | 46 | 46 | 46 | 46 | 46 | 46 |
| 0 | 24 | 24 | 24 | 24 | 24 | 24 | 25 | 27 |

*(table continues — values on lower rows: 12, 5, 2, 0 across columns with variations 12/12/12/12/12/12/13/14, 5/5/5/5/6/7/9, 2/2/2/3/4/, etc.)*

COMBINATION COMPRISING AT LEAST ONE SPLICEOSOME MODULATOR AND AT LEAST ONE INHIBITOR CHOSEN FROM BCL2 INHIBITORS, BCL2/BCLXL INHIBITORS, AND BCLXL INHIBITORS AND METHODS OF USE

This application is a national stage filing under 35 U.S.C. § 371 of International Application No. PCT/US2018/058277, filed on Oct. 30, 2018, which claims priority from U.S. Provisional Application No. 62/579,666, filed Oct. 31, 2017, and U.S. Provisional Application No. 62/580,364, filed Nov. 1, 2017. The contents of which are each hereby incorporated by reference in their entirety.

The instant application contains a Sequence Listing that is submitted herewith electronically in ASCII format and is hereby incorporated by reference in its entirety. Said ASCII copy, created on Feb. 4, 2019, is named SequenceListing.txt and is 3,414 bytes in size. Please insert the Sequence Listing filed herewith into the application before the claims. In connection with said Sequence Listing, the undersigned hereby states that: 1. The sequence listing, filed herewith in accordance with 37 C.F.R. §§ 1.821-1.825, does not include new matter; and 2. The attached ASCII-format sequence listing serves as both a written copy and the computer readable copy of the Sequence Listing; thus, the contents of the written and the computer readable copies of the Sequence Listing are the same.

The BCL2 family genes encode BH domain-containing anti-apoptotic/pro-survival proteins, which play a particularly important role in regulating apoptosis. There are at least five BCL2 proteins, BCL2, BCL2L1, BCL2L2, BCL2A1 and MCL1, which are involved in tumor cell survival in a variety of cancer types (see, e.g., Delbridge A R D, et al., 2016, Nat. Rev. Cancer 16, 99-109; Czabotar P E, et al., 2014, Nat. Rev. Mol. Cell Bio. 15, 49-63). Several compounds have been developed to inhibit the BCL2 family proteins, including, for example, ABT199 (venetoclax), ABT263 (navitoclax), A-1331852, and ABT737. While BCL2 inhibitors have shown promise as cytotoxic agents, these compounds are unable to inhibit the anti-apoptotic effects of MCL1. Particularly, MCL1 is focally amplified in many cancer types (Zack T I, et al., 2013, Nature Genet. 45, 1134-1140). It has been reported that high BCL2L1 (BCLxL) expression confers resistance to MCL1 repression, and MCL1 amplification/overexpression is the major mechanism conferring resistance to BCL2, BCL2/BCLxL, and BCLxL inhibitors (see, e.g., Wei G, et al., 2012, Cancer Cell 21(4): 547-562; Lin X, et al., 2007, Oncogene 26(27): 3972-3979; Teh T C, et al, 2017, Leukemia. doi: 10.1038/leu.2017.243). Effective therapies to overcome resistance to BCL2, BCL2/BCLxL, and BCLxL inhibitors are needed.

A growing body of evidence indicates that combination therapies can help overcome incomplete response and therapeutic resistance of single agent treatment of cancer. (Sellers W R., 2011, Cell 147(1): 26-31.) For example, the combination of MAPK pathway inhibitors vemurafenib (RAF inhibitor) and cobimetinib (MEK inhibitor) has been approved by the FDA for treating melanoma patients bearing B-RAF mutations. (Flaherty K T, et al., 2012, N Engl J Med 367:1694-1703.) However, development of efficacious combination therapies has been challenging partially due to lack of efficient preclinical approaches that are predictive of clinical combination activity, particularly for evidence-based drug combinations. Mechanism-based drug combination strategies have been applied in preclinical and clinical settings by relying on target- and pathway-related biological findings from basic research. Given the complexity of mechanisms of action, there have been many obstacles to identifying effective combinations for cytotoxic agents.

SUMMARY

The present disclosure is based on the observation that the combination of certain spliceosome modulators (e.g., pladienolide compounds) and BCL2, BCL2/BCLxL, or BCLxL inhibitors shows improved (e.g., synergistic) anticancer effects. Pladienolide compounds that target the spliceosome and mutations therein are particularly useful. Thus, provided herein are combination therapies for treating cancer comprising administering a therapeutically effective amount of at least one pladienolide spliceosome modulator (e.g., E7107 and/or H3B-8800) and a therapeutically effective amount of at least one inhibitor chosen from BCL2, BCL2/BCLxL, and BCLxL inhibitors.

Methods, combination therapies, pharmaceutical compositions, and kits for treating cancer using a combination of a therapeutically effective amount of at least one pladienolide spliceosome modulator (e.g., E7107 and/or H3B-8800) and a therapeutically effective amount of at least one inhibitor chosen from BCL2, BCL2/BCLxL, and BCLxL inhibitors are also provided.

Other features of the present disclosure will be apparent from the following detailed description, the drawings, and the claims.

BRIEF DESCRIPTION OF THE DRAWINGS

FIG. 1 depicts a Western Blot Analysis of MCL1L (full-length MCL1) and GAPDH (loading control). Lysates dilution was used as semi-quantification standards.

FIG. 2 depicts the growth inhibition of cell lines upon knockdown of MCL1 by shRNA. CNTRL: Control shRNA; Dox: doxycycline.

FIG. 3 is a schematic representation of MCL gene splicing.

FIG. 4 depicts quantitative RT-PCR detection of MCL1 mRNAs: MCL1L: long form containing exons 1, 2 and 3; MCL1S: short form contains exons 1 and 3; MCL1 pre-mRNA: mRNA with intron 1 retention.

FIG. 5 depicts a Western Blot Analysis of MCL1L (full-length), truncated MCL1, cleaved PARP, and tubulin (loading control) after treatment with E7107 for 6 hours.

FIG. 6 depicts inducible cDNA expression of MCL1L in NCIH1568 cells. Western Blot Analysis showed the expression of MCL1L and GAPDH (loading control). CNTRL: control vector.

FIG. 7 depicts growth inhibition of NCIH1568 cell lines with empty vector (control) and MCL1L cDNA overexpression.

FIG. 8 depicts inducible shRNA mediated knockdown of BCLxL (encoded by BCL2L1) in A549 cells. Western Blot Analysis showed the expression of BCLxL and GAPDH (loading control).

FIG. 9 depicts growth inhibition of A549 cell lines upon Dox-induced knockdown of BCLxL. Dox: doxycycline.

Figure 1:
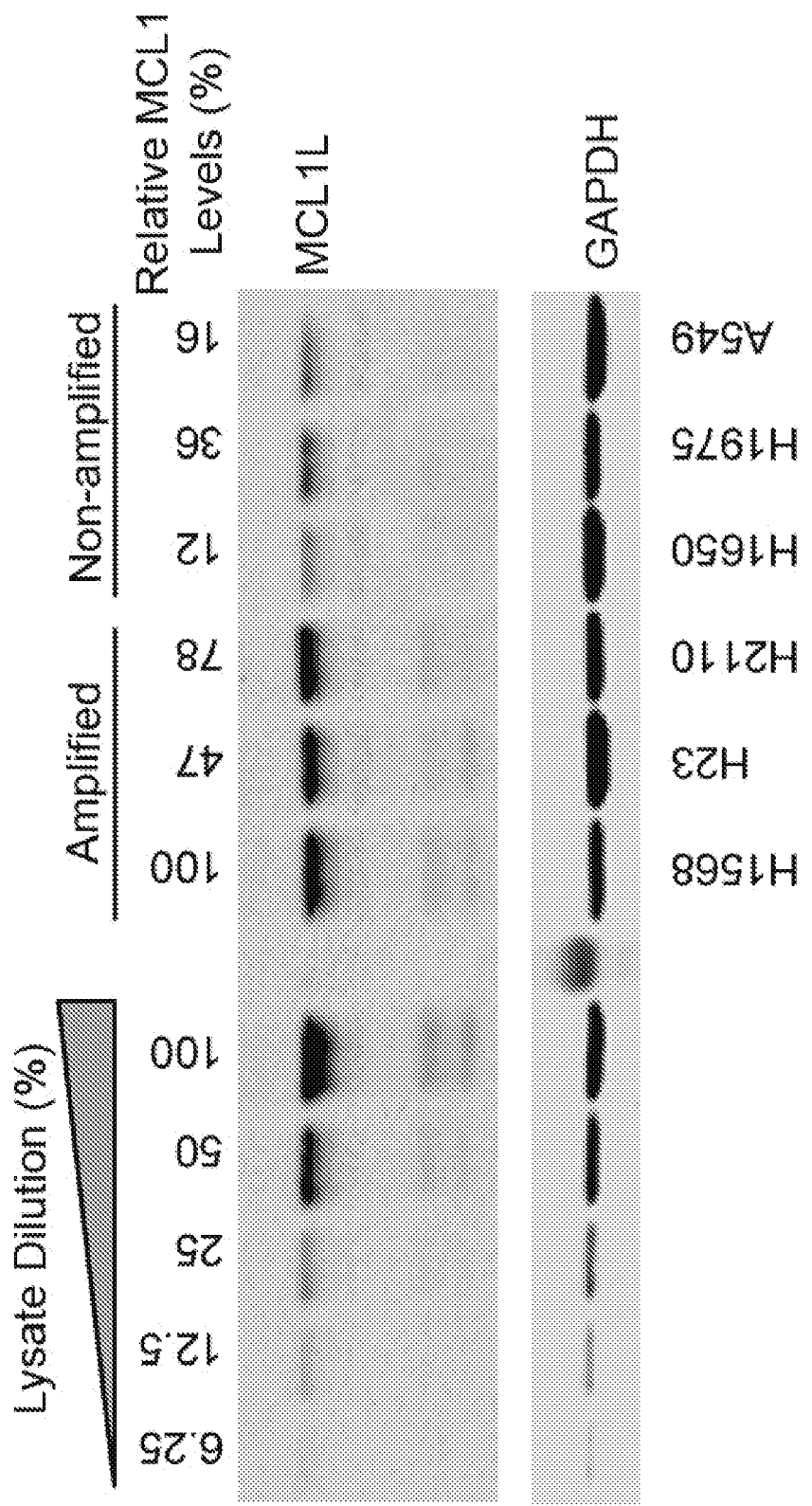
FIGS. 1 and 2 show the identification of MCL1 overexpressed and MCL1 dependent non-small cell lung carcinoma (NSCLC) cell lines.

As used herein, the following definitions shall apply unless otherwise indicated.

"Isomers" refers to compounds having the same number and kind of atoms, and hence the same molecular weight, but differing with respect to the arrangement or configuration of the atoms. "Stereoisomers" refers to compounds that have the same atomic connectivity but different arrangements of their atoms in space. "Diastereoisomers" or "diastereomers" refers to stereoisomers that are not enantiomers. "Enantiomers" refers to stereoisomers that are non-superimposable mirror images of one another. "Geometric isomers" refers to cis-trans isomers having different positions of groups with respect to a double bond or ring or central atom.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the opposite enantiomer, of the compound. A typical stereomerically pure compound comprises greater than about 80% by weight of one stereoisomer of the compound and less than about 20% by weight of the other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Treatment," "treat," or "treating" cancer refers to reversing (e.g., overcoming a differentiation blockage of the cells), alleviating (e.g., alleviating one or more symptoms, such as fatigue from anemia, low blood counts, etc.), and/or delaying the progression of (e.g., delaying the progression of the condition such as transformation to AML) a cancer as described herein.

"Subject", as used herein, means an animal subject, preferably a mammalian subject, and particularly human beings.

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol, and wool fat.

A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al., "Commentary: Occurrence of Pharmaceutically Acceptable Anions and Cations in the Cambridge Structural Database," J. Pharmaceutical Sciences, vol. 94, no. 10 (2005), and Berge et al., "Pharmaceutical Salts", J. Pharmaceutical Sciences, vol. 66, no. 1 (1977), which are incorporated by reference herein.

Unless otherwise stated, compounds depicted herein may include mixtures of the compound depicted herein and any of enantiomeric, diastereomeric, and/or geometric (or conformational) forms of the structure; for example, the R and S configurations for each asymmetric center, (Z) and (E) double bond isomers, and (Z) and (E) conformational isomers. Unless otherwise stated, compounds depicted herein coexisting with tautomeric forms are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds may be useful, for example, as analytical tools or probes in biological assays.

Various pladienolide compounds have been developed as splicing modulators for the treatment of cancer, including those disclosed in the following patent applications: WO 2002/060890; WO 2004/011459; WO 2004/011661; WO 2004/050890; WO 2005/052152; WO 2006/009276; WO 2008/126918; and WO 2015/175594, each of which are incorporated herein by reference. For example, a pladienolide compound (8E,12E,14E)-7-((4-Cycloheptylpiperazin-1-yl)carbonyl)oxy-3,6,16,21-tetrahydroxy-6,10,12,16,20-pentamethyl-18,19-epoxytricosa-8,12,14-trien-11-olide, also known as E7107, is a semisynthetic derivative of the natural product pladienolide D, and the results of its Phase I study have been reported:

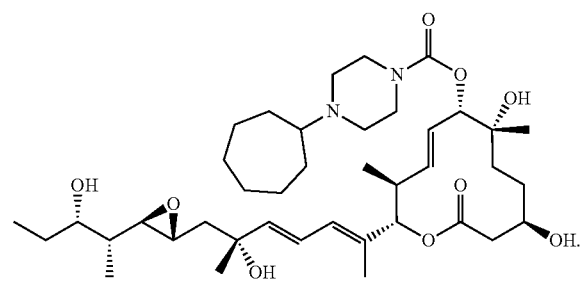 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(C3CCCCCC3)CC2)/C=C/[C@@H]1C]

As another example, the pladienolide pyridine compound (2S,3S,6S,7R,10R,E)-7,10-dihydroxy-3,7-dimethyl-12-oxo-2-((R,2E,4E)-6-(pyridin-2-yhhepta-2,4-dien-2-yl)oxacyclododec-4-en-6-yl 4-methylpiperazine-1-carboxylate (also named "(2S,3S,4E,6S,7R,10R)-7,10-dihydroxy-3,7-dimethyl-12-oxo-2-((2E,4E,6R)-6-(pyridin-2-yhhepta-2,4-dien-2-yl)oxacyclododec-4-en-6-yl 4-methylpiperazine-1-carboxylate"), also known as H3B-8800, has received orphan drug designation for the treatment of certain hematological cancers and has the following structure:

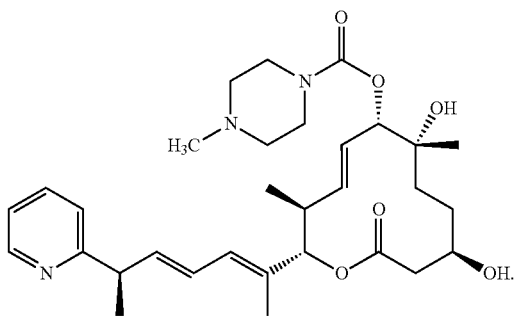 [SMILES: C/C(=C\C=C\[C@@H](C)c1ccccn1)[C@H]1OC(=O)C[C@H](O)CC[C@@](C)(O)[C@@H](OC(=O)N2CCN(C)CC2)/C=C/[C@@H]1C]

In some embodiments, the at least one pladienolide spliceosome modulator for use in combination therapy is chosen from a compound of formula 1 ("E7107"):

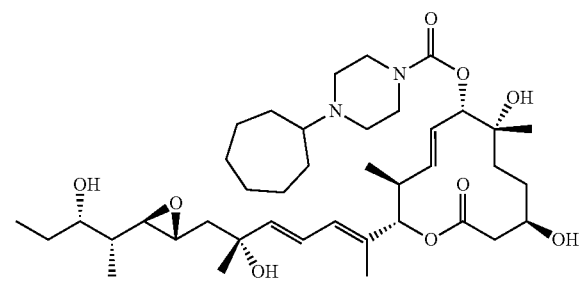 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(O)[C@@H](OC(=O)N2CCN(C3CCCCCC3)CC2)/C=C/[C@@H]1C]

and pharmaceutically acceptable salts thereof.

In some embodiments, the at least one pladienolide spliceosome modulator for use in combination therapy is chosen from a compound of formula 2 ("H3B-8800"):

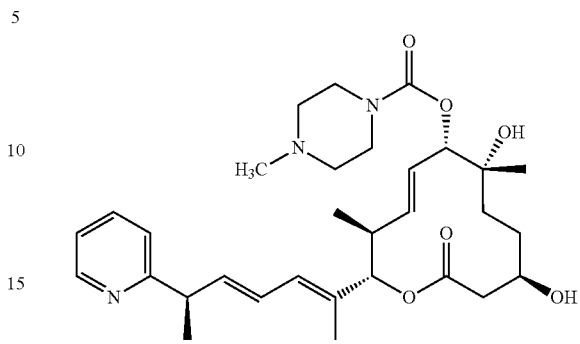

and pharmaceutically acceptable salts thereof.

As used herein, the at least one inhibitor chosen from BCL2, BCL2/BCLxL, and BCLxL inhibitors include, but are not limited to, HA14-1, BH3I-1, antimycin A, chelerythrine, gossypol (NSC19048), apogossypol (NSC736630), TW-37, 4-(3-methoxy-phenylsulfonyl)-7-nitro-benzofuran-3-oxide (MNB), TM12-06, obatoclax (GX15-070), venetoclax (ABT199), navitoclax (ABT263), A-1331852, and ABT737.

In some embodiments, the at least one inhibitor chosen from BCL2, BCL2/BCLxL, and BCLxL inhibitors is chosen from venetoclax (ABT199), navitoclax (ABT263), A-1331852, ABT737, and pharmaceutically acceptable salts thereof.

The methods disclosed herein may be used to treat various types of cancers, including hematological malignancies and solid tumors.

Hematological malignancies may include cancers of the blood (e.g., leukemia) or cancers of the lymph nodes (e.g., lymphomas) or other related cancers. Leukemias may include acute lymphoblastic leukemia (ALL), acute myelogenous leukemia (AML), chronic lymphocytic leukemia (CLL), chronic myelogenous leukemia (CML), Chronic myelomonocytic leukemia (CMML), acute monocytic leukemia (AMoL), etc. Lymphomas may include Hodgkin's lymphoma and non-Hodgkin's lymphoma. Other hematologic malignancies may include myelodysplastic syndrome (MDS) and multiple myeloma (MM).

Solid tumors may include carcinomas such as adenocarcinoma, e.g., breast cancer, pancreatic cancer, prostate cancer, colon or colorectal cancer, lung cancer (including non-small cell lung carcinoma (NSCLC) and small cell lung carcinoma (SCLC)), gastric cancer, cervical cancer, endometrial cancer, ovarian cancer, cholangiocarcinoma, glioma, melanoma, and the like.

The methods disclosed herein may also be used to treat cancers that may be responsive to agents that target a spliceosome gene or protein, e.g., SF3B1. Examples of such cancers include, but are not limited to, myelodysplastic syndrome, multiple myeloma, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, or lung cancer (including non-small cell lung carcinoma (NSCLC) and small cell lung carcinoma (SCLC)). Exemplary spliceosome genes or proteins include, but are not limited to, splicing factor 3B subunit 1 (SF3B1), U2 small nuclear RNA auxiliary factor 1 (U2AF1), serine/arginine-rich splicing factor 2 (SRSF2), zinc finger (CCCH type) RNA-binding motif and serine/arginine rich 2 (ZRSR2), pre-mRNA-processing-splicing factor 8 (PRPF8), U2 small nuclear RNA auxiliary factor 2 (U2AF2), splicing factor 1 (SF1), splicing factor 3a subunit 1 (SF3A1), PRP40 pre-mRNA processing factor 40 homolog B (PRPF40B), RNA binding motif protein 10 (RBM10), poly(rC) binding protein 1 (PCBP1), crooked neck pre-mRNA splicing factor 1 (CRNKL1), DEAH (Asp-Glu-Ala-His) box helicase 9 (DHX9), peptidyl-prolyl cis-trans isomerase-like 2 (PPIL2), RNA binding motif protein 22 (RBM22), small nuclear ribonucleoprotein Sm D3 (SNRPD3), probable ATP-dependent RNA helicase DDX5 (DDX5), pre-mRNA-splicing factor ATP-dependent RNA helicase DHX15 (DHX15), and polyadenylate-binding protein 1 (PABPC1).

The methods disclosed herein may also be used to treat MCL1-dependent cancers. Examples of MCL1-dependent cancers may include, but are not limited to, multiple myeloma, leukemias, lymphomas, and solid tumors. MCL1-dependent leukemias may include, but are not limited to, acute lymphoblastic leukemia, acute myelogenous leukemia, chronic lymphocytic leukemia, chronic myelogenous leukemia, chronic myelomonocytic leukemia, and acute monocytic leukemia. MCL1-dependent lymphomas may include, but are not limited to, Hodgkin's lymphoma and non-Hodgkin's lymphoma. MCL1-dependent solid tumors may include, but are not limited to, lung cancer (e.g., non-small cell lung carcinoma and small cell lung carcinoma), breast cancer, pancreatic cancer, prostate cancer, colon or colorectal cancer, gastric cancer, cervical cancer, endometrial cancer, ovarian cancer, cholangiocarcinoma, glioma, and melanoma.

It has been shown that cancers with high expression of MCL1 are sensitive to MCL1 inhibition by either direct target inhibition or gene level perturbation, e.g. transcriptional or splicing inhibition (Gao Y, Koide K., 2013, ACS Chem Biol. 8(5): 895-900; Wei G, et al., 2012, Cancer Cell 21(4): 547-562). It has also been indicated that high BCL-xL expression confers resistance to MCL1 repression, and MCL1 amplification/overexpression is the major mechanism conferring resistance to BCL2/xL inhibitors (see, e.g., Wei G, et al., 2012, Cancer Cell 21(4): 547-562; Lin X, et al., 2007, Oncogene 26(27): 3972-3979; Teh T C, et al, 2017, Leukemia. doi: 10.1038/leu.2017.243). Without wishing to be bound by any particular theory, as described herein, pladienolide derivatives E7107 and H3B-8800 may induce potent splicing modulation of MCL1 gene, leading to reduced expression of the functional full-length protein. Decreased MCL1 protein may cause robust cell death in cancer cell lines. The combination of at least one pladienolide derivative (e.g., E7107 and/or H3B-8800) and the at least one inhibitor chosen from BCL2, BCL2/BCLxL, and BCLxL inhibitors may induce synergistic growth inhibition of cancer cells. Thus, the combination of at least one small molecule splicing modulators and the at least one inhibitor chosen from BCL2, BCL2/BCLxL, and BCLxL inhibitors may be used to treat cancers such as those dependent on anti-apoptotic genes.

Also disclosed herein are pharmaceutical compositions comprising at least one pladienolide spliceosome modulator and at least one inhibitor chosen from BCL2, BCL2/BCLxL, and BCLxL inhibitors. In some embodiments, the pharmaceutical composition further comprises at least one pharmaceutically acceptable carrier. The at least one pharmaceutically acceptable carrier may be chosen according to the intended route of administration.

The pharmaceutical compositions disclosed herein may be formulated for parenteral, oral, inhalation spray, topical, rectal, nasal, buccal, vaginal or implanted reservoir administration, etc. The term "parenteral" as used herein includes subcutaneous, intravenous, intramuscular, intra-articular, intra-synovial, intrasternal, intrathecal, intrahepatic, intralesional and intracranial injection or infusion techniques. In particular embodiments, the compounds of the combination therapy are administered intravenously, orally, subcutaneously, or via intramuscular administration. Sterile injectable forms of the compositions of the present disclosure may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

For oral administration, the at least one pladienolide spliceosome modulator and/or at least one inhibitor chosen from BCL2, BCL2/BCLxL, and BCLxL inhibitors may be provided in an acceptable oral dosage form, including, but not limited to, capsules, tablets, aqueous suspensions or solutions. In the case of tablets for oral use, carriers may be chosen from, for example, lactose and corn starch. Lubricating agents, such as magnesium stearate, may also be added. For oral administration in a capsule form, useful diluents include lactose and dried cornstarch. When aqueous suspensions are required for oral use, the active ingredient is combined with an emulsifying and/or suspending agent. If desired, certain sweetening, flavoring or coloring agents may also be added.

In some embodiments, at least one pladienolide spliceosome modulator and at least one inhibitor chosen from BCL2, BCL2/BCLxL, and BCLxL inhibitors disclosed herein are administered to a subject in a single dosage form or by separate or sequential administration of each active agent.

In some embodiments, at least one pladienolide spliceosome modulator and at least one inhibitor chosen from BCL2, BCL2/BCLxL, and BCLxL inhibitors are formulated into tablets, pills, capsules, or solutions. In some embodiments, at least one pladienolide spliceosome modulator and/or at least one inhibitor chosen from BCL2, BCL2/BCLxL, and BCLxL inhibitors are formulated into a solution for parenteral administration. In some embodiments, the at least one pladienolide spliceosome modulator and at least one inhibitor chosen from BCL2, BCL2/BCLxL, and BCLxL inhibitors are formulated in segregated regions or distinct caplets of housed within a capsule. In some embodiments, at least one pladienolide spliceosome modulator and at least one inhibitor chosen from BCL2, BCL2/BCLxL, and BCLxL inhibitors are formulated in isolated layers in a tablet.

In some embodiments, the pharmaceutical composition comprises: a therapeutically effective amount of at least one pladienolide spliceosome modulator, a therapeutically effective amount of at least one inhibitor chosen from BCL2, BCL2/BCLxL, and BCLxL inhibitors, and at least one pharmaceutically acceptable carrier.

In some embodiments, the pharmaceutical composition comprises: a therapeutically effective amount of E7107, a therapeutically effective amount of at least one inhibitor chosen from BCL2, BCL2/BCLxL, and BCLxL inhibitors, and at least one pharmaceutically acceptable carrier.

In some embodiments, the pharmaceutical composition comprises: a therapeutically effective amount of H3B-8800, a therapeutically effective amount of at least one inhibitor chosen from BCL2, BCL2/BCLxL, and BCLxL inhibitors, and at least one pharmaceutically acceptable carrier.

In some embodiments, the at least one pladienolide spliceosome modulator and at least one inhibitor chosen from BCL2, BCL2/BCLxL, and BCLxL inhibitors may be administered as separate compositions and optionally as different forms, e.g., as separate tablets or solutions. Further as a non-limiting example, both the at least one pladienolide spliceosome modulator and at least one inhibitor chosen from BCL2, BCL2/BCLxL, and BCLxL inhibitors may be administered, separately, as oral tablets.

In some embodiments, the at least one pladienolide spliceosome modulator and at least one inhibitor chosen from BCL2, BCL2/BCLxL, and BCLxL inhibitors are to be administered as separate compositions:
  a pharmaceutical composition comprising a therapeutically effective amount of at least one inhibitor chosen from BCL2, BCL2/BCLxL, and BCLxL inhibitors and at least one pharmaceutically acceptable carrier; and
  a pharmaceutical composition comprising a therapeutically effective amount of at least one pladienolide spliceosome modulator and at least one pharmaceutically acceptable carrier.

In some embodiments, provided herein is a kit comprising a first pharmaceutical composition comprising a therapeutically effective amount of at least one pladienolide spliceosome modulator, a second pharmaceutical composition comprising a therapeutically effective amount of at least one inhibitor chosen from BCL2, BCL2/BCLxL, and BCLxL inhibitors, and instructions for use of the kit in the treatment of cancer.

In some embodiments, the at least one pladienolide spliceosome modulator and at least one inhibitor chosen from BCL2, BCL2/BCLxL, and BCLxL inhibitors are administered simultaneously. In some embodiments, the at least one pladienolide spliceosome modulator and at least one inhibitor chosen from BCL2, BCL2/BCLxL, and BCLxL inhibitors are administered sequentially. In some embodiments, the at least one pladienolide spliceosome modulator and at least one inhibitor chosen from BCL2, BCL2/BCLxL, and BCLxL inhibitors are administered intermittently. The length of time between administrations of the at least one pladienolide spliceosome modulator and at least one inhibitor chosen from BCL2, BCL2/BCLxL, and BCLxL inhibitors may be adjusted to achieve the desired therapeutic effect. In some embodiments, the at least one pladienolide spliceosome modulator and at least one inhibitor chosen from BCL2, BCL2/BCLxL, and BCLxL inhibitors are administered only a few minutes apart. In some embodiments, the at least one pladienolide spliceosome modulator and at least one inhibitor chosen from BCL2, BCL2/BCLxL, and BCLxL inhibitors are administered several hours (e.g., about 2, 4, 6, 10, 12, 24, or 36 h) apart. In some embodiments, it may be advantageous to administer more than one dosage of one of the at least one pladienolide spliceosome modulator and at least one inhibitor chosen from BCL2, BCL2/BCLxL, and BCLxL inhibitors between administrations of the remaining therapeutic agent. For example, one therapeutic agent may be administered at 1 hour and then again at 11 hours following administration of the other therapeutic agent. In some embodiments, the therapeutic effects of each pladienolide spliceosome modulator and BCL2, BCL2/BCLxL, or BCLxL inhibitor should overlap for at least a portion of the duration, so that the overall therapeutic effect of the combination therapy may be attributable in part to the combined or synergistic effects of the combination therapy.

The at least one pladienolide spliceosome modulator and at least one inhibitor chosen from BCL2, BCL2/BCLxL, and BCLxL inhibitors disclosed herein may be administered to a subject in a treatment effective or therapeutically effective amount. The amount of each of at least one pladienolide spliceosome modulator and at least one inhibitor chosen from BCL2, BCL2/BCLxL, and BCLxL inhibitors that may be combined with at least one pharmaceutically acceptable carrier to produce a single dosage form will vary depending upon the subject treated and the intended route of administration.

In some embodiments, the pharmaceutical compositions are formulated so that a dosage from 0.01 to 100 mg/kg body weight/day of each of the at least one pladienolide spliceosome modulator and at least one inhibitor chosen from BCL2, BCL2/BCLxL, and BCLxL inhibitors is administered to a subject. In some embodiments, a dosage ranging from 1 to 100 mg/kg body weight/day of each of the at least one pladienolide spliceosome modulator and at least one inhibitor chosen from BCL2, BCL2/BCLxL, and BCLxL inhibitors is administered to a subject. In some embodiments, a dosage ranging from 0.01 mg to 50 mg of each of the at least one pladienolide spliceosome modulator and at least one inhibitor chosen from BCL2, BCL2/BCLxL, and BCLxL inhibitors is administered to a subject. In some embodiments, a dosage ranging from 1 mg to 50 mg, from 0.1 mg to 25 mg, or from 5 mg to 40 mg, of each of the at least one pladienolide spliceosome modulator and at least one inhibitor chosen from BCL2, BCL2/BCLxL, and BCLxL inhibitors is provided.

In some embodiments, the at least one pladienolide spliceosome modulator is administered in a dosage range of 1 mg/kg to 10 mg/kg. In some embodiments, the at least one pladienolide spliceosome is administered at a dosage of 1 mg/kg, 1.25 mg/kg, 2 mg/kg, 2.5 mg/kg, 3 mg/kg, 4 mg/kg, 5 mg/kg, 6 mg/kg, 7 mg/kg, 8 mg/kg, 9 mg/kg, or 10 mg/kg. In some embodiments, the at least one pladienolide spliceosome is administered at a dosage of 5 mg/kg. In some embodiments, the at least one pladienolide spliceosome is administered at a dosage of 8 mg/kg.

In some embodiments, E7107 is administered intravenously at a dosage of 5 mg/kg for five consecutive days. In some embodiments, H3B-8800 is administered orally at a dosage of 8 mg/kg for five consecutive days followed by a nine-day rest.

One of ordinary skill will understand that a specific dosage and treatment regimen for any particular patient will depend upon a variety of factors, including the activity of the specific compound employed, the age, body weight, general health, sex, diet, time of administration, rate of excretion, drug combination, the judgment of the treating physician, and the severity of the particular disease being treated. The amount of each active agent of the combination therapy will also depend upon the particular compound/salt in the composition.

The following examples are set forth so that the embodiments described herein, and uses thereof, may be more fully understood. It should be understood that these examples are for illustrative purposes only and are not to be construed as limiting in any manner.

EXAMPLES

A. Materials and Methods
1. Cell Lines and Cell Culture Protocol

The Non-Small Cell Lung Cancer (NSCLC) cell lines A549, NCI-H23, NCI-H1568, NCI-H1650, NCI-H1975, and NCI-H2110 were obtained from the American Type Culture Collection (ATCC) and cultured as per manufacturers instruction. Inducible shRNA and cDNA lines generated by lentiviral transduction were cultured according to manufacturer's instructions utilizing Tet System Approved FBS (Clontech) rather than standard sera. LentiX-293T (Clontech) was used for the generation of shRNA and cDNA overexpression viruses for infection and cultured according to the manufacturers instruction. The cell lines were tested for mycoplasma contamination and authenticated to confirm cell identity. Puromycin (0.25-1.25 µg/ml, Thermo Fisher Scientific) was used for selection of shRNA expressing cells; G418 (0.5-2 mg/mL, Thermo Fisher Scientific) was used for selection of inducible cDNA expressing cells. Doxycycline Hyclate (Sigma) (Dox) was used for induction of the shRNA and cDNA.

NKM1 and K052 cells are obtained from Japanese Collection of Research Bioresources Cell Bank. HNT34, MONOMAC6 and MUTZ3 cells are obtained from Deutsche Sammlung von Mikroorganismen and Zellkulturen. HNT34 and NKM1 cells are maintained in RPMI (ATCC) with 10% fetal bovine serum. K052 cells are maintained in Alpha-MEM (ATCC) with 10% fetal bovine serum. MONOMAC6 cells are maintained in RPMI (ATCC) with 20% fetal bovine serum. MUTZ3 cells are maintained in Alpha-MEM (ATCC) with 20% fetal bovine serum and 20% conditioned 5637 medium. The cell lines are incubated in a humidified incubator at 37° C. with 5% $CO_2$.

2. Western Blot Analysis of MCL1 and BCLxL Protocol

Cell lines were lysed in RIPA buffer (Boston BioProducts) plus protease-inhibitor cocktail (Mini-complete, EDTA-free, Roche) and phosphatase inhibitor PhosSTOP (Roche). Lysates were diluted in RIPA buffer with 4×LDS Sample Buffer (Nupage, Thermo Fisher Scientific) and 10× Reducing Reagent (Nupage, Thermo Fisher Scientific) and boiled for 5 minutes. Twenty five micrograms of protein were loaded per well in 4-12% Bis-Tris SDS Page gels (Novex, Thermo Fisher Scientific). Gels were transferred to nitrocellulose membranes using iBlot system (Thermo Fisher Scientific). Membranes were blocked in blocking buffer (1× Tris-Buffered Saline+0.1% Tween-20 (Boston Bioproducts)+5% Non-Fat Dry Milk (Bio-Rad)) for 1 hour and then cut. Each section was probed separately with antibodies to each of the following proteins in blocking buffer: MCL1 (Cell Signaling Technologies 5453) (D35A5) rabbit monoclonal diluted 1:500, BCL-xL (Cell Signaling Technologies 2764) (54H6) rabbit monoclonal diluted 1:500, Cleaved Parp (Cell Signaling Technologies 5625) (D64P10) rabbit monoclonal diluted 1:500, and GAPDH (Sigma G8795) mouse monoclonal at 100 ng/mL. Blots were incubated with primary antibodies dilutions shaking at 4° C. overnight. Western blots were then blotted either with Odyssey Licor or HRP secondary antibodies. Blots were then washed four times using wash buffer (1× Tris-Buffered Saline+0.1% Tween-20). Blots imaged using Licor were probed shaking at room temperature for 1 hour with Licor IR-labeled secondary antibodies, IRDye® 800CW Goat anti-Rabbit IgG (Odyssey 925-32211) and IRDye® 680LT Goat anti-Mouse IgG (Odyssey 925-68020) diluted 1:10,000 in blocking buffer. Blots were then washed three times with wash buffer. IR-dye detection was performed using the Licor imaging system (Odyssey) according to manufacturer's instruction. Blots imaged using HRP were probed shaking at room temperature for 1 hour with Anti-mouse IgG, HRP-linked Antibody (Cell Signaling Technologies 7076) and Anti-rabbit IgG, HRP-linked Antibody (Cell Signaling Technologies 7074) diluted 1:5000 in blocking buffer. Blots were then washed three times with wash buffer. HRP detection was performed using SuperSignal West Femto Maximum Sensitivity Substrate (Thermo Fisher Scientific) and imaged with ImageQuant™ LAS 4000 biomolecular imager (GE Healthcare Life Sciences) according to manufacturer's instruction.

3. Quantitative Real-Time PCR of MCL1 Protocol

RNA lysates were isolated from cells treated with compounds in 96 well plates and reverse transcribed using TaqMan Gene Expression Cells-to-CT Kit (Thermo Fisher Scientific) according to manufacturer's instruction. Quantitative PCR was performed using TaqMan Gene Expression Master Mix (Thermo Fisher Scientific) with MCL1 transcript probes (Integrated DNA technologies FAM-ZEN/IBFQ) duplexed with 18S rRNA VIC-PL (Thermo Fisher Scientific assay ID Hs99999901_s1) and quantified using the ΔΔCt method.

```
MCL1L probe set
    primer       ATATGCCAAACCAGCTCCTAC primer       AAGGACAAAACGGGACTGG probe        AGAACTCCACAAACCCATCCCAGC MCL1S probe set
    primer       AAAGCCAATGGGCAGGT primer       CCACCTTCTAGGTCCTCTACAT probe        TCCACAAACCCATCTTGGAAGGCC MCL1 pre-mRNA intron1-exon2 probe set
    primer       GACAAAGGAGGCCGTGAGGA primer       GTTTGTTACGCCGTCGCTGAAA probe        TCAGGCATGCTTCGGAAACTGGA
```

4. Inducible shRNA and cDNA Protocol

BCL-xL shRNA 1 (GCTCACTCTTCAGTCGGAAAT) (Wei G, et al., 2012, Cancer Cell 21(4): 547-562) was cloned into AgeI and EcoRI of the Tet inducible lentiviral pLKO-iKD-H1 puro vector (Wiederschain D, et al., 2009, Cell Cycle 8(3): 498-504). MCL1 shRNA 48 (GCATCGAAC- CATTAGCAGAAA) (Wei G, et al., 2012, Cancer Cell 21(4): 547-56) was cloned into Agel and EcoRl of the Tet inducible lentiviral pLKO-iKD-U6 puro vector. MCL1-L pENTR-D-TOPO was Gateway cloned (LR clonase, Thermo Fisher Scientific) into pINDUCER20 (Meerbrey K L, et al., 2011, Proc Natl Acad Sci USA. 108(9):3665-3670). Lentiviruses were prepared in LentiX-293T cells. 2.5M cells in 10 cm Biocoat Collagen II dishes (Corning) were transfected with 2.4 µg of target pLKO-shRNA or pINDUCER20 plasmid, plus 2.4 µg of pΔ8.91 (packaging), and 0.6 µg VSVG (envelope) using TransiT reagent (Mirus). pINDUCER20+MCL1-L, pINDUCER20 vector, pLKO-iKD-U6 puro+MCL1 shRNA 48 and pLKO-iKD-U6 puro vector viruses were used to infect A549, NCI-H23, NCI-H1568, NCI-H1650, NCI-H1975, and NCI-H2110. pLKO-iKD-H1 puro+BCL-xL shRNA 1 and pLKO-iKD-H1 puro viruses were used to infect A549, NCI-H23, NCI-H1568, and NCI-H2110. Cells were infected with or without spin infection using Polybrene (Millipore). One to three days after infection, the cells were cultured in Geneticin (pINDUCER20) or Puromycin (pLKO shRNAs). The selected cells were cultured in the presence or absence of Dox (300 ng/ml). Cells were harvested for protein and RNA three to five days post induction. RNA was isolated as in the MCL1 real time PCR section. Protein extracts were prepared as in MCL1 and BCL-xL Western Blot Procedure section above.

5. Cell Viability and MCL1 Rescue Protocol

For inducible shRNA experiments, cells were cultured in 96 well with or without 300 ng/mL Dox for 72 hours and then lysed with CellTiter-Glo Luminescent Cell Viability Assay (Promega) according to manufacturer's instruction and analyzed using Perkin-Elmer Envision. Dox treated wells were normalized to no treatment for each cell line.

For compound dose response experiments, cells were plated in 96 or 384 well plates at 1,000 cells in 50 µl per well. Compounds were added from an 11-point serial dilution series in 90% DMSO to cells in media by acoustic transfer. The final DMSO concentration was 0.1%. The plates were lidded and the cells were allowed to grow at 37° C. and 5% $CO_2$. At t=0, untreated cells were lysed with CellTiter-Glo and measured on an Envision plate reader. At t=72 (72 hours after compound addition), cells treated with compound were lysed with CellTiter-Glo and analyzed on Envision. The luminescence value from each treatment sample was normalized to the average value of the respective DMSO control.

For MCL1 rescue experiments, cell lines were cultured for 72 hours with 300 ng/mL dox, then sub-cultured and seeded into 96 or 384 well plates with 300 ng/mL dox.

6. Combination Studies

Compound serial dilutions were performed for a splicing modulator (e.g., E7107 or H3B-8800) and a BCL2, BCL2/BCLxL, or BCLxL inhibitor (e.g., ABT263, ABT199, or A-1331852), and cells were treated as discussed in the Cell Viability and MCL1 rescue protocol. For BCL-xL knockdown, cells were treated with 300 ng/mL dox as per the Cell Viability and MCL1 rescue protocol prior to seeding 384 well plates. Final DMSO concentration was 0.2%. CellTiter-Glo was performed as per Cell Viability and MCL1 rescue protocol. Data was analyzed using Chalice Bioinformatics software (Horizon Discovery, Cambridge, UK). To estimate compound synergy for a splicing modulator (e.g., E7107 or H3B-8800) and a BCL2, BCL2/BCLxL, or BCLxL inhibitor (e.g., ABT263, ABT199, or A-1331852), Horizon Discovery's Loewe Additivity model was used, and Loewe Excess was calculated by subtracting the Loewe Model (pure additivity based on compound self-cross) from the Dose-Response matrix.

7. Animal Studies

To identify the tolerated doses to use for the combination arm of the efficacy study, mice are administered spliceosome modulator (e.g., E7107 or H3B-8800) intravenously once a day for 5 consecutive days (QDx5) at well-tolerated dose levels (e.g., 1.25, 2.5 and 5 mg/kg for E7107) or the BCL2, BCL2/BCLxL, or BCLxL inhibitor orally once a day (QD) at tolerated doses (100, 50 and 25 mg/kg) alone or in combination. After dosing, the animals are monitored until health problem develop (e.g., paralysis or excessive body weight loss). The maximal tolerated combination dose and the respective single doses of each compound are used in the efficacy study in tumor-bearing animals.

The antitumor activity of the combination of E7107 and BCL2, BCL2/BCLxL, or BCLxL inhibitor is evaluated in vivo in a subcutaneous model of A549 and NCIH1568. Cells (H1568 $5\times10^6$ and A549 $10\times10^6$ cells) are subcutaneously implanted into the flank of nude mice. Animals are administered spliceosome modulator and a BCL2, BCL2/BCLxL, or BCLxL inhibitor based on the doses identified in the previous study.

B. Results

1. Identification of MCL1-Overexpressed and MCL1-Dependent NSCLC Cell Lines

Figure 2:
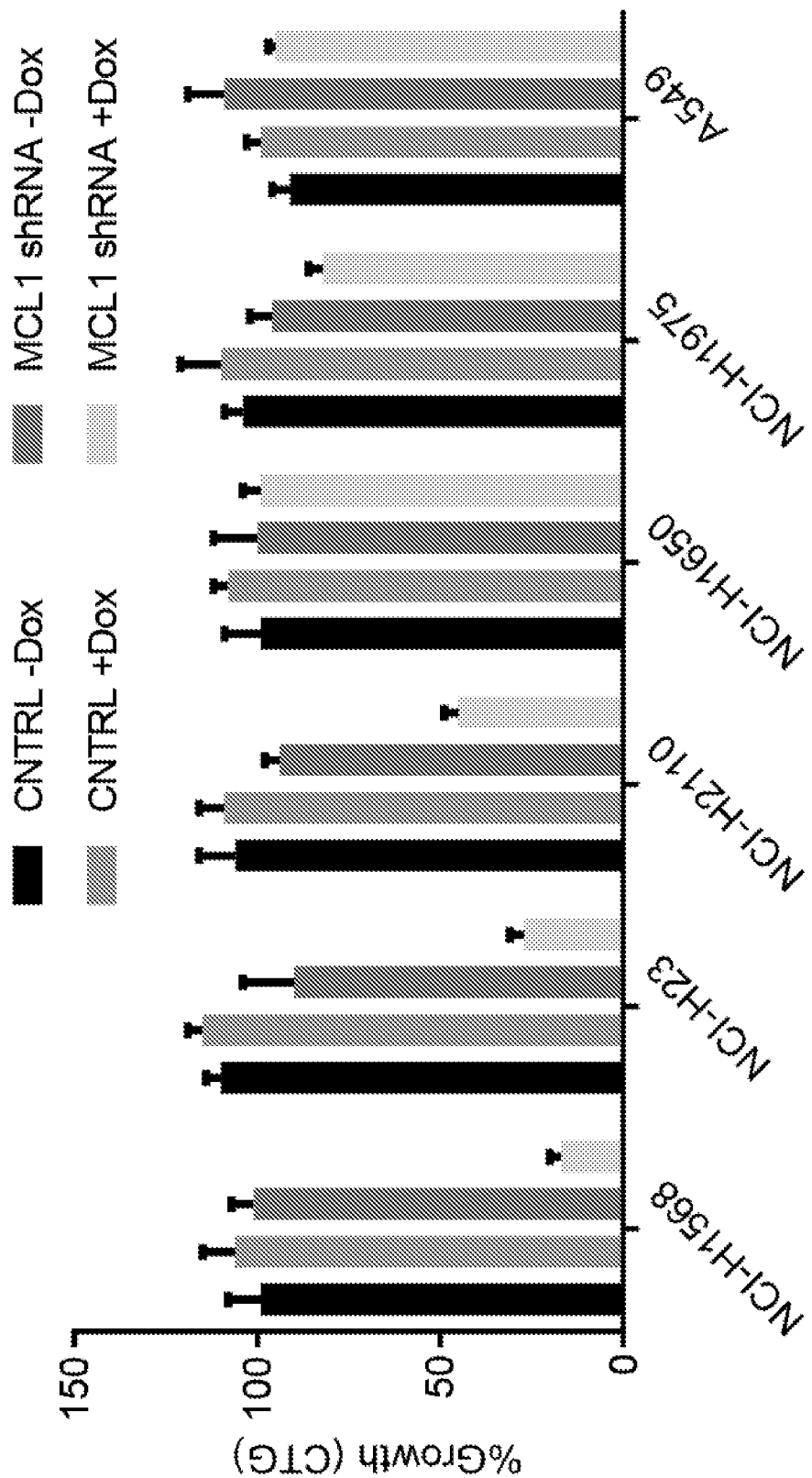

In order to identify the cell line models to evaluate the combinatory activity of pladienolide spliceosome modulators and BCL2, BCL2/BCLxL, or BCLxL inhibitors, six non-small cell lung carcinoma (NSCLC) cell lines with or without MCL1 amplification were selected based on a previous report (Wei G, et al., 2012, Cancer Cell 21(4): 547-562). Western Blot Analysis was conducted for MCL1 protein expression in these cell lines. As shown in FIG. 1, MCL1 gene-amplified NCIH1568, NCIH23 and NCIH2110 express higher levels of MCL1 proteins expression in comparison with non-amplified cell lines NCIH1650, NCIH1975 and A549. Next, the dependence on MCL1 was tested in these cell lines using an inducible shRNA that specifically downregulates MCL1, demonstrating a selective MCL-dependence in MCL1-amplified but not non-amplified cell lines (FIG. 2). MCL1-overexpressed and MCL1-dependent NSCLC cell line models were identified for use in further functional studies.

2. E7107 Induces Splicing Modulation of MCL1

Figure 3:
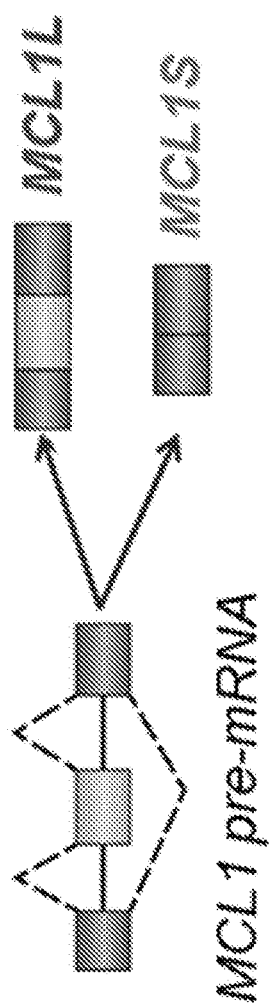
FIGS. 3-5 show E7107 induces splicing modulation of MCL1 in NCIH1568 cells.
Figure 4:
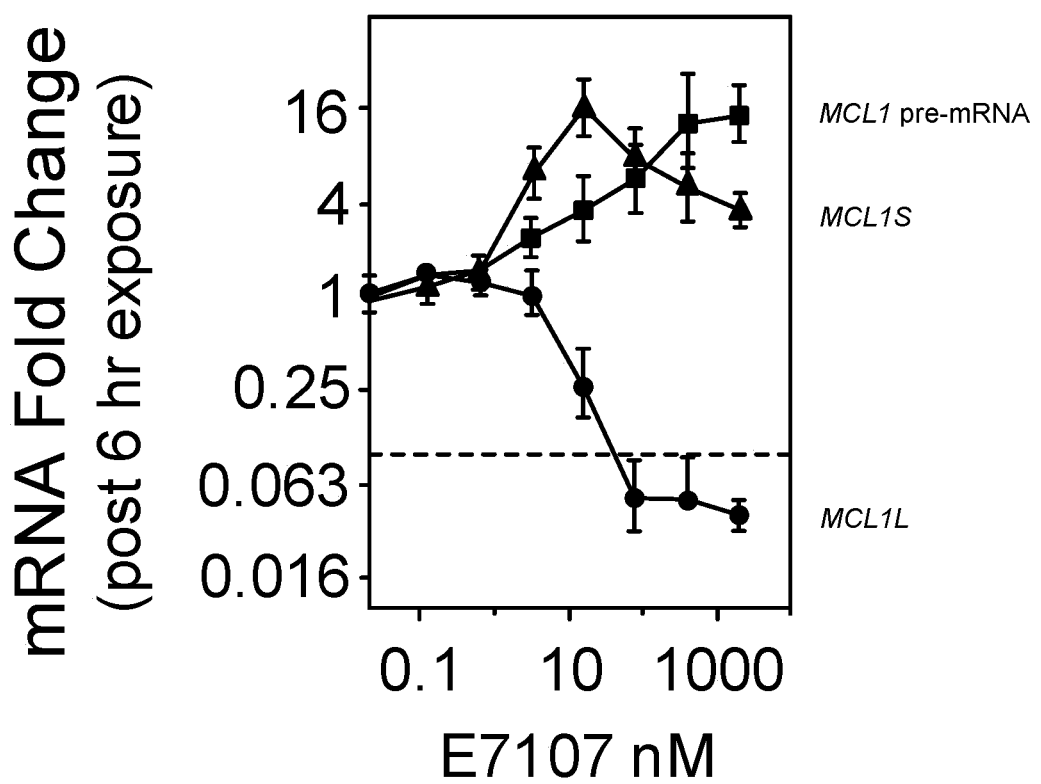

The splicing modulation of the MCL1 gene by pladienolide derivative E7107 was studied. The MCL1 gene contains three exons and two introns that can be alternatively spliced to two major transcripts: MCL1L that encodes the functional full-length protein and MCL1S that encodes a putative loss-of-function protein (FIG. 3). As part of the study, the intron-retention of MCL1 was measured since E7107 perturbs the splicing machinery. Six-hour treatment of the NCIH1568 cells with E7107 induced robust reduction of MCL1L mRNA, transient expression of MCL1S mRNA, and continuous induction of the MCL1 pre-mRNA with intron-retention (FIG. 4).

Figure 5:
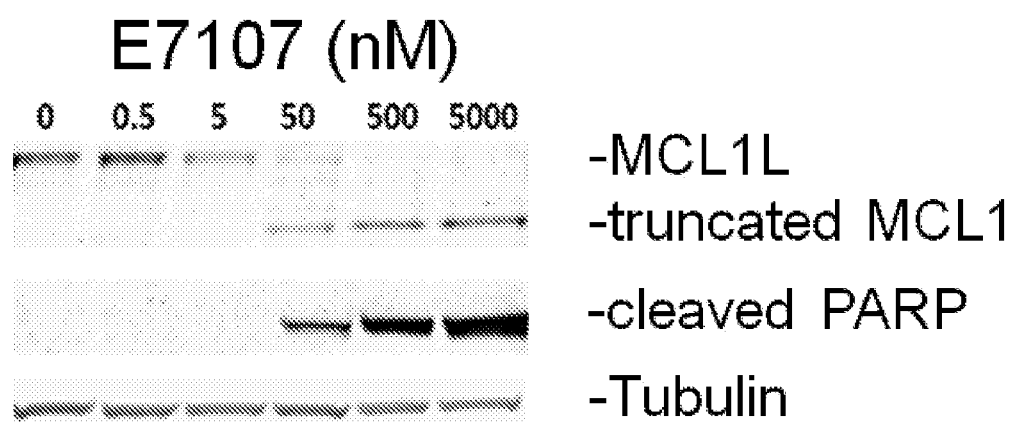

The protein expression of MCL1 was further tested in NCIH1568 cells. Consistent with the mRNA data, E7107 triggered a dose-dependent downregulation of the full length MCL1 protein, whereas a truncated short-form protein product was increased in a dose-dependent manner. The alteration of MCL protein levels was associated with an induction of the cleaved PARP protein which is an indicator of apoptosis, suggesting that splicing modulation of MCL1 by E7107 may cause cell death in NCIH1568 cells (FIG. 5).

3. E7107-Induced Cell Death is MCL1 and BCLxL Dependent

Figure 6:
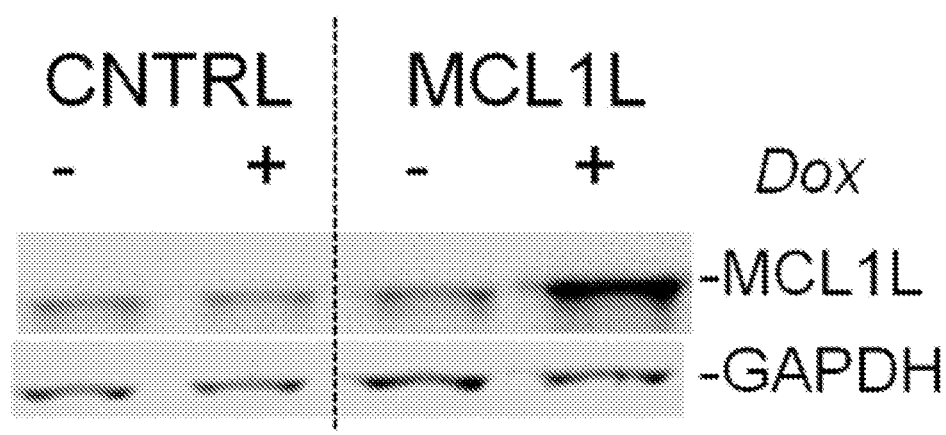
FIGS. 6-9 show E7107-induced cytotoxicity is MCL1- and BCLxL-dependent.
Figure 7:
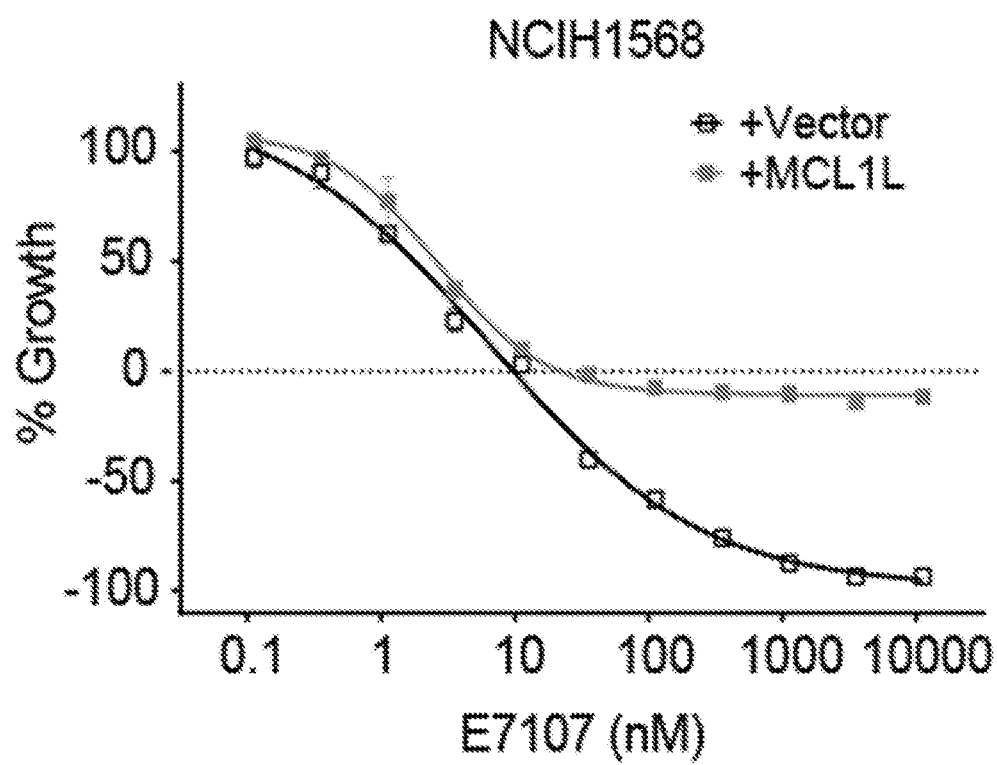
Figure 8:
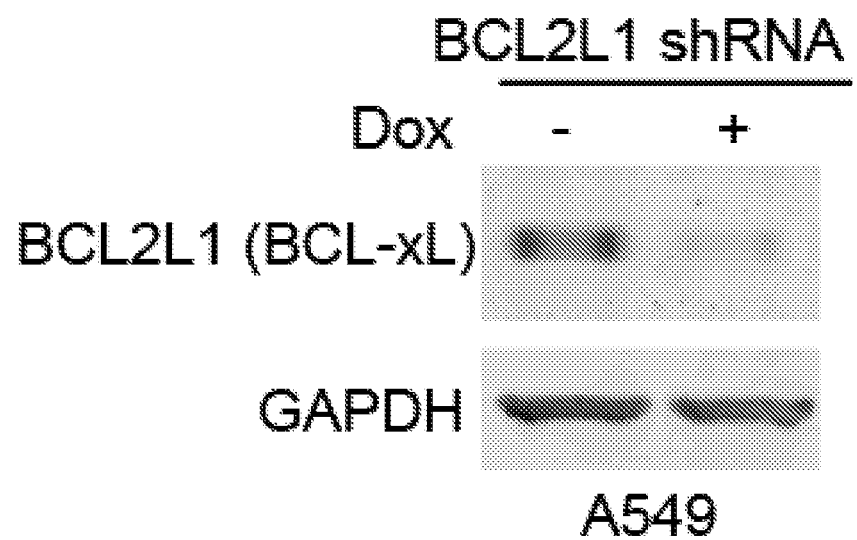
Figure 9:
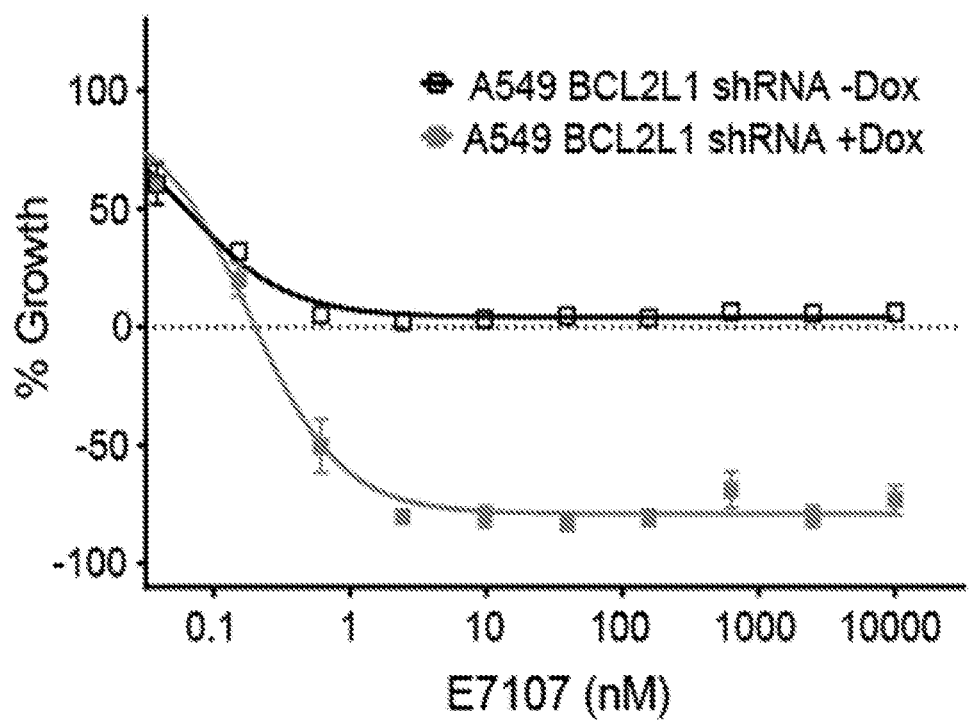

To confirm E7107-induced downregulation of MCL1 is the cause of cell death, MCL1L cDNA was overexpressed in NCIH1568 cells, as shown by the Western Blot Analysis (FIG. 6). The cDNA overexpression of MCL1L rescued the cell death induced by E7107 in the MCL1-dependent cell line (FIG. 7). The role of BCLxL (encoded by BCL2L1) in E7107-treated MCL1-independent A549 cells was further explored. While E7107 only induced a cytostatic inhibition as expected, inducible knockdown of BCLxL (FIG. 8) led to a clear cell death upon E7107-treatment (FIG. 9). In summary, these data support that inhibition of both MCL1 and BCLxL results in synergistic activity leading to cytotoxicity in both MCL1-dependent and independent cancer cells.

4. Combination of E7107 with BCL2, BCL2/BCLxL, or BCLxL Inhibitors Demonstrates Synergistic Effect Since E7107 can modulate MCL1, and other BCL2 proteins may counter the cytotoxicity induced by MCL1 inhibition, the combination of E7107 with BCL2, BCL2/BCLxL, or BCLxL inhibitors may provide enhanced cell death through broad targeting of all anti-apoptotic BCL2 proteins.

Figure 10:
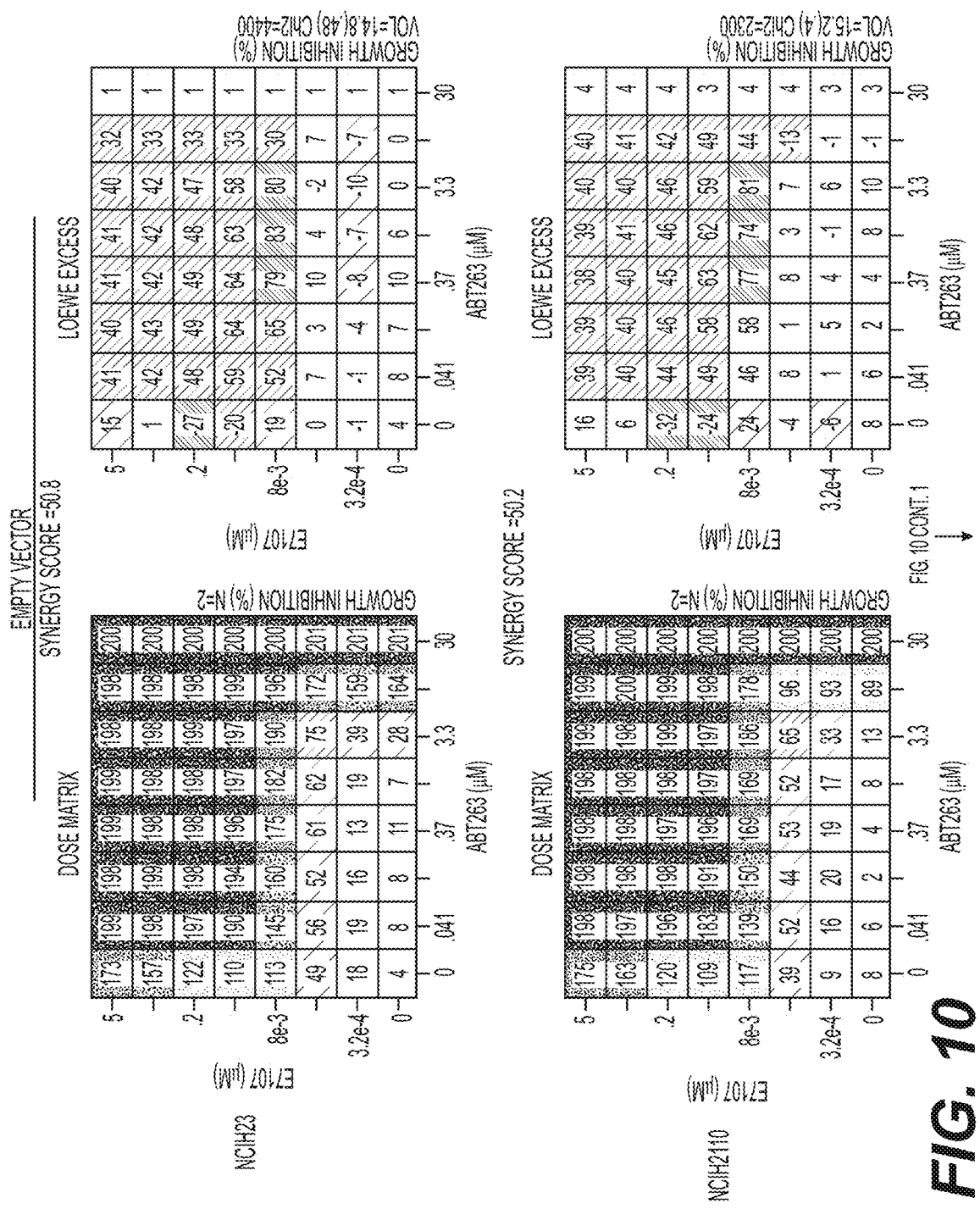
FIG. 10 shows the synergistic effect of treatment with E7107 and ABT263 in four NSCLC cell lines. This study was performed in vector control or BCLxL shRNA.
Figure 10:
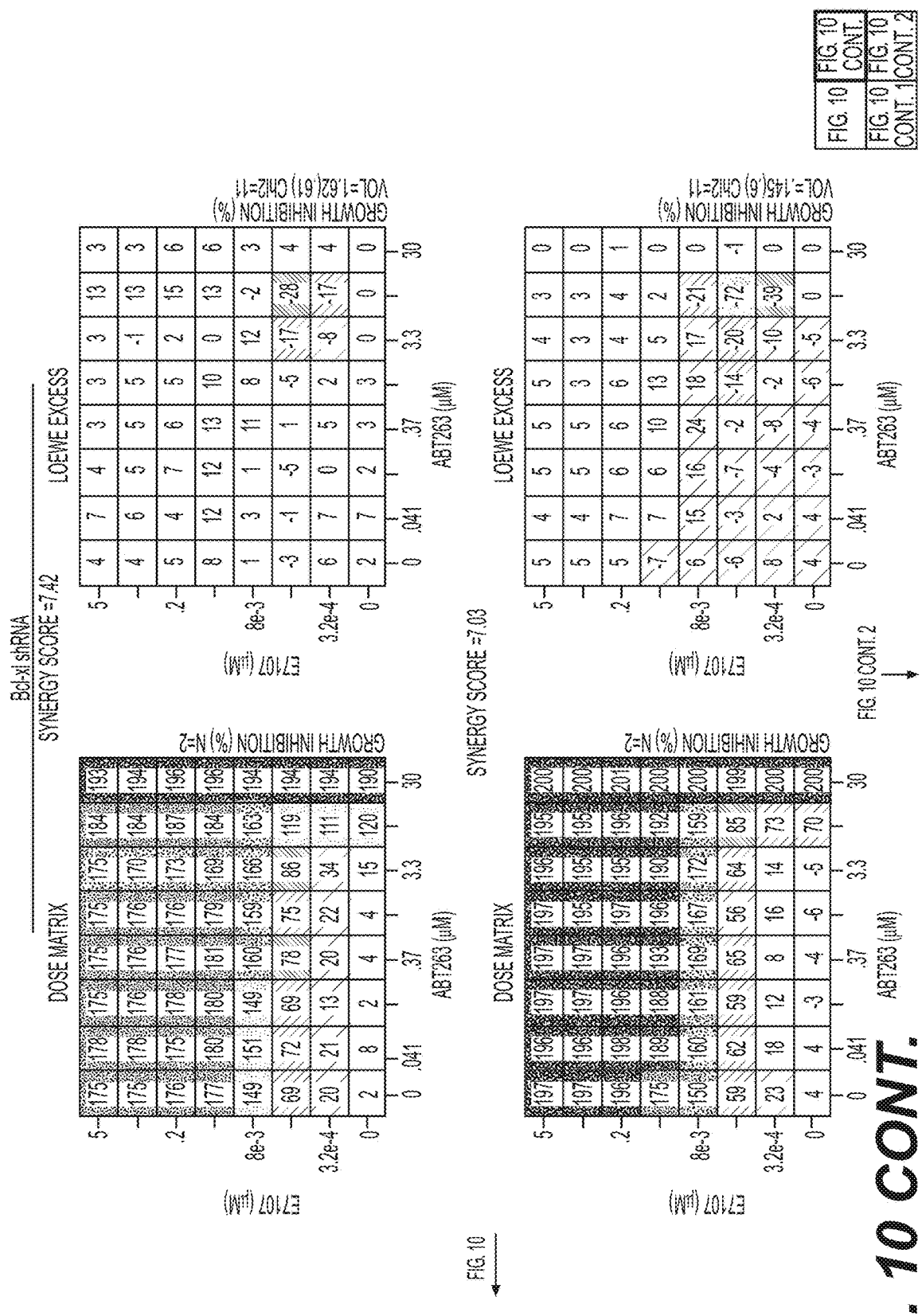
Figure 10:
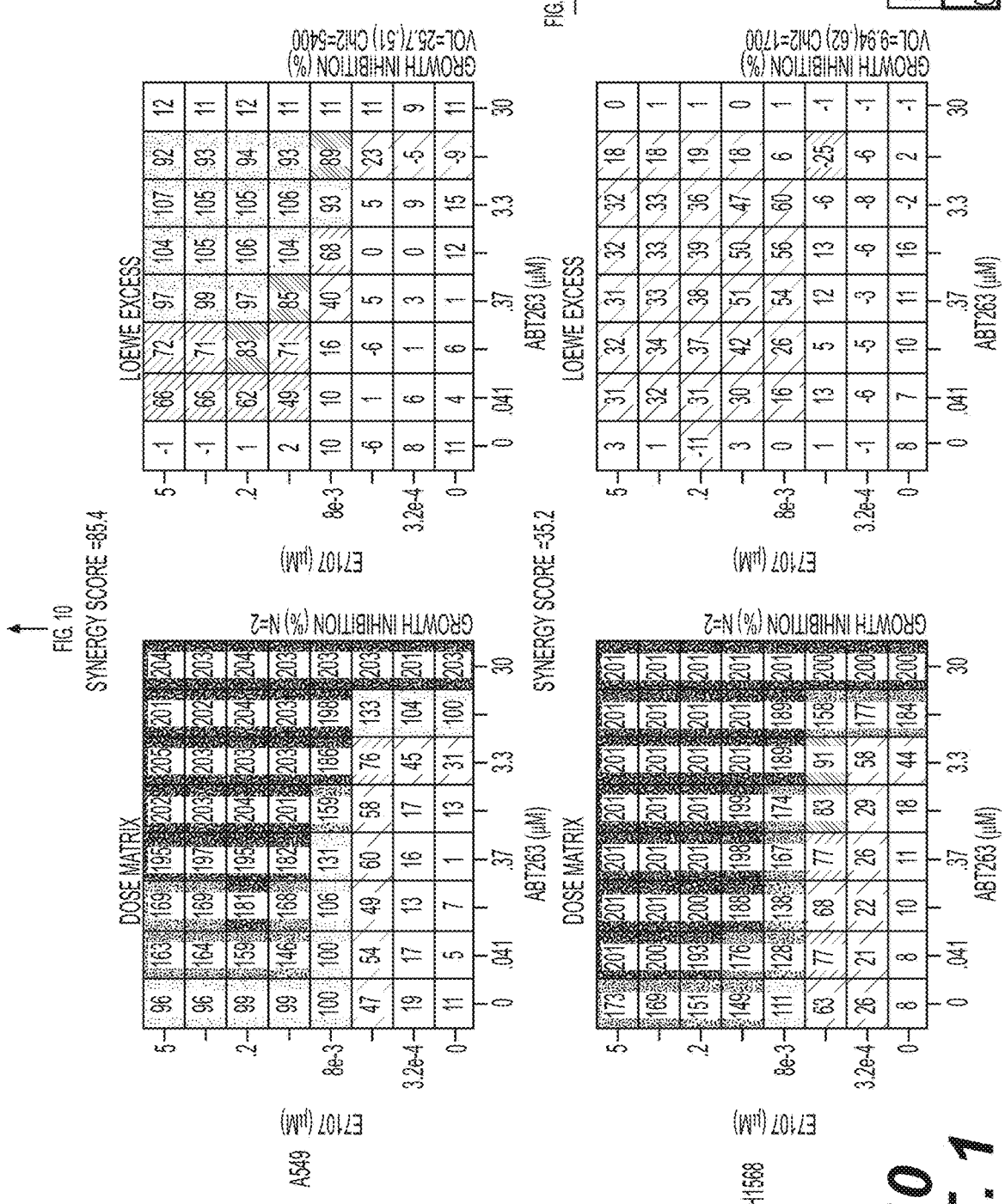
Figure 10:
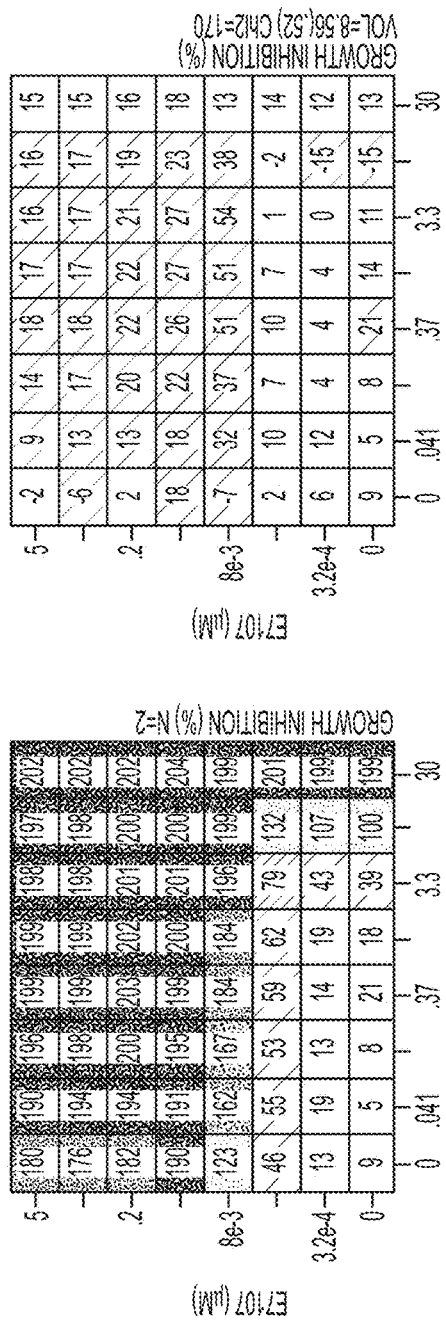
Figure 10:
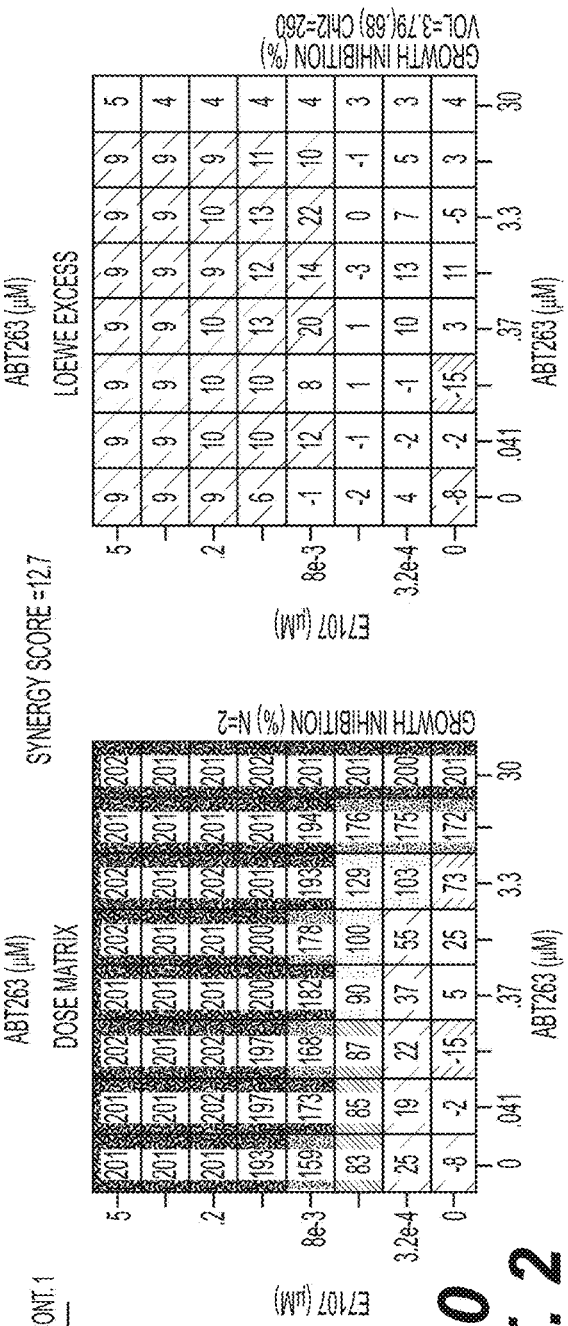

ABT263 (Navitoclax), a BCL2/BCLxL/BCLw pan inhibitor, was tested in combination with E7107 in an 8×8 dose matrix mode (FIG. 10). Indeed, combination of the two inhibitors showed strong synergistic effect with large excess over the Loewe additivity model (FIG. 10, left panels) in four different empty vector expressing cell line models including MCL1-dependent NCIH23 (synergy score=50.8), NCIH2110 (synergy score=50.2), NCIH1568 (synergy score=35.2) and MCL1-independent A549 cells (synergy score=85.4). Moreover, shRNA depletion of BCLxL largely diminished this synergy between E7107 and ABT263 (FIG. 10, right panels), confirming that the genetic shRNA manipulation and pharmacological inhibitor (ABT263) impinged on the same node BCLxL to achieve the synergistic effect. Specifically, the synergy score are greatly reduced in NCIH23 (7.42), NCIH2110 (7.03), NCIH1568 (12.7) and A549 (28.3).

Figure 11:
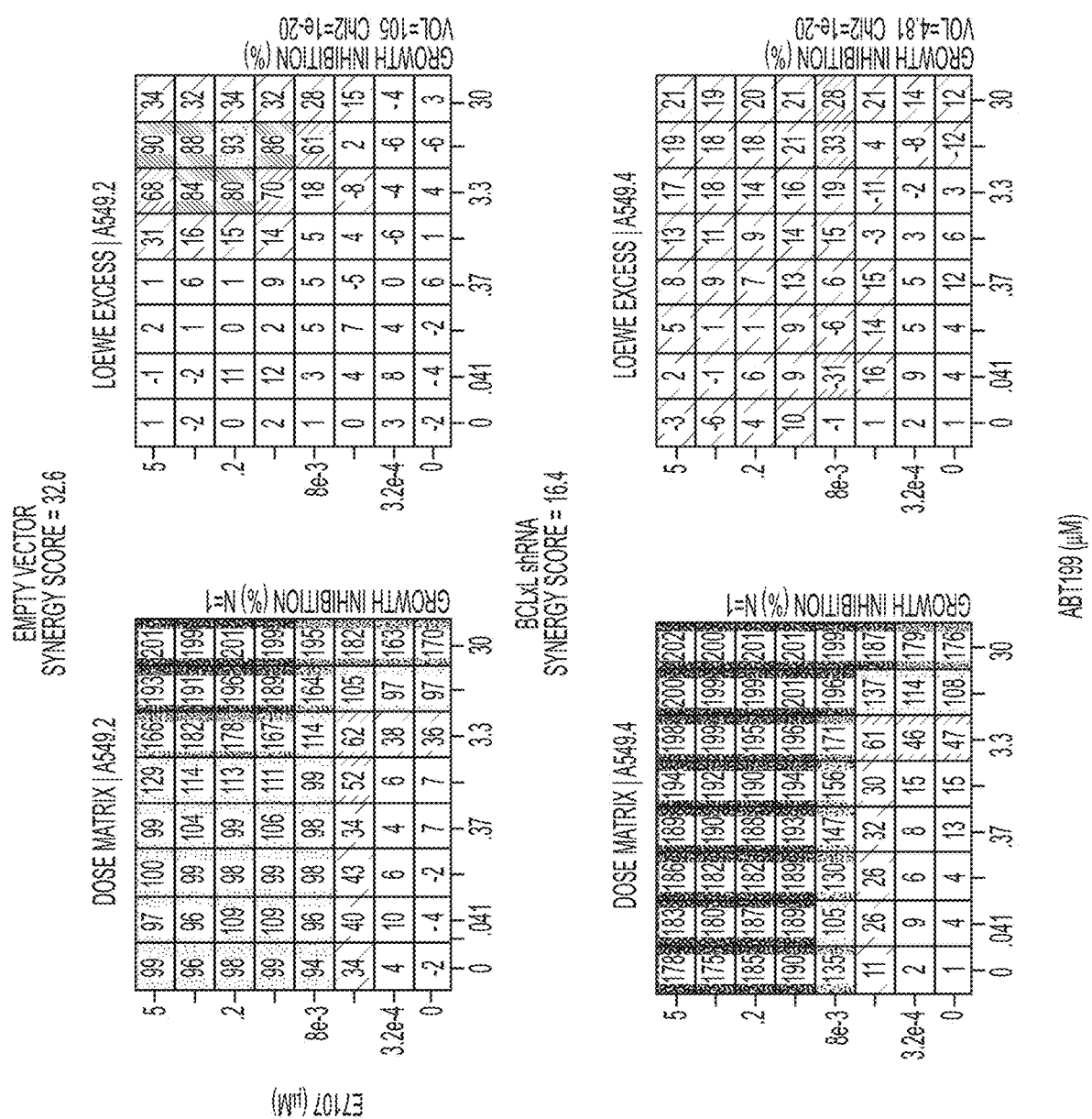
FIG. 11 shows the synergistic effect of treatment with E7107 and ABT199 in the A549 cell line. This study was performed in vector control or BCLxL shRNA.

ABT199 (venetoclax) was also tested in combination with E7107. ABT199 is a more BCL2-selective inhibitor that is active on BCLxL. Combination of E7107 and ABT199 in MCL1-independent A549 cells demonstrated a synergistic activity (score=32.6), whereas knockdown of BCLxL greatly reduced the synergism (score=16.4) (FIG. 11).

5. Combination of H3B-8800 with BCL2, BCL2/BCLxL, or BCLxL Inhibitors Demonstrates Synergistic Effect H3B-8800, another SF3b-targeting splicing modulator, was also evaluated for the potential synergistic activity with BCL2/BCLxL inhibitors, which may provide enhanced cell death through broad targeting of all anti-apoptotic BCL2 proteins.

Figure 12:
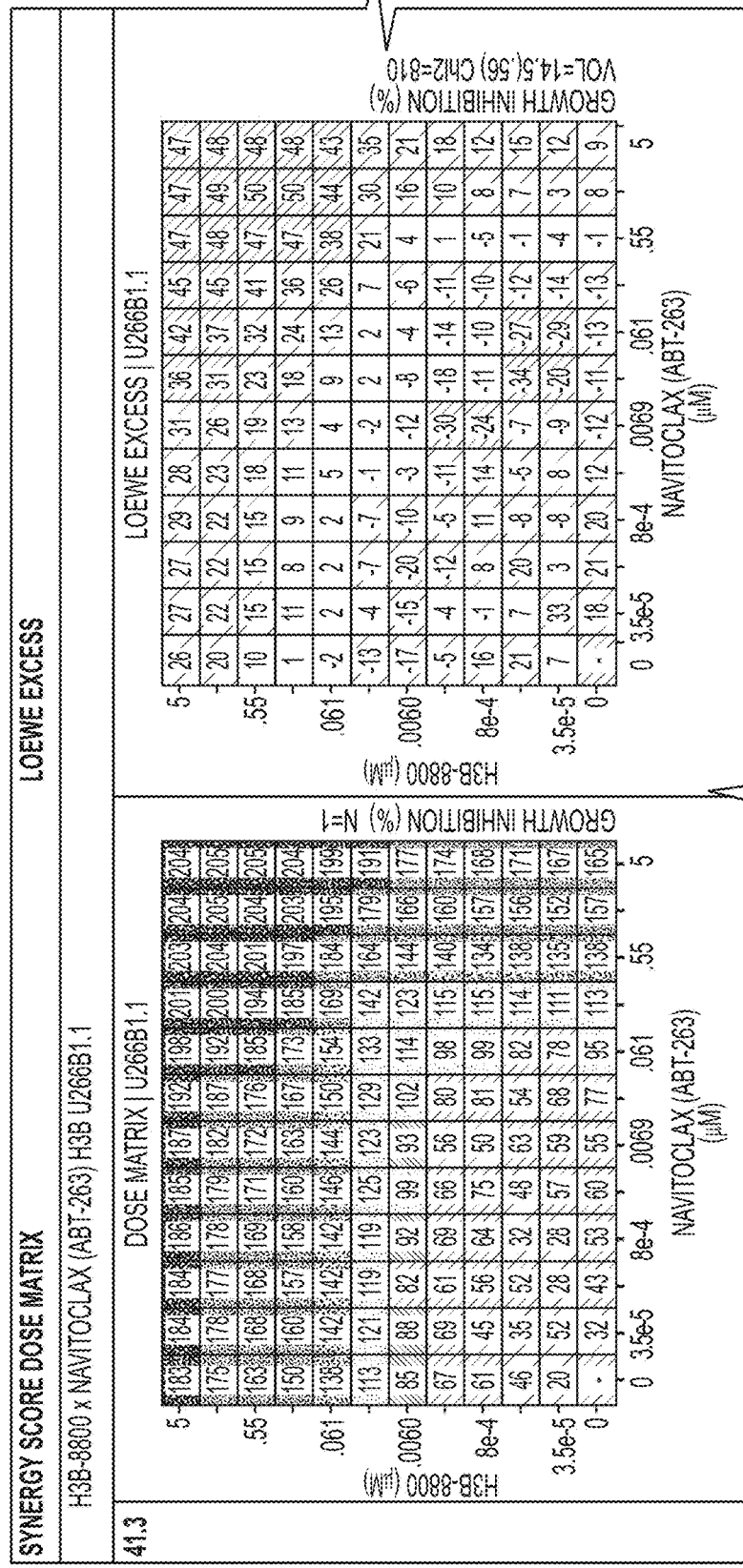
FIG. 12 shows the synergistic effect of treatment with H3B-8800 and ABT263 in two multiple myeloma cell lines: U266B1 and RPMI8226.
Figure 12:
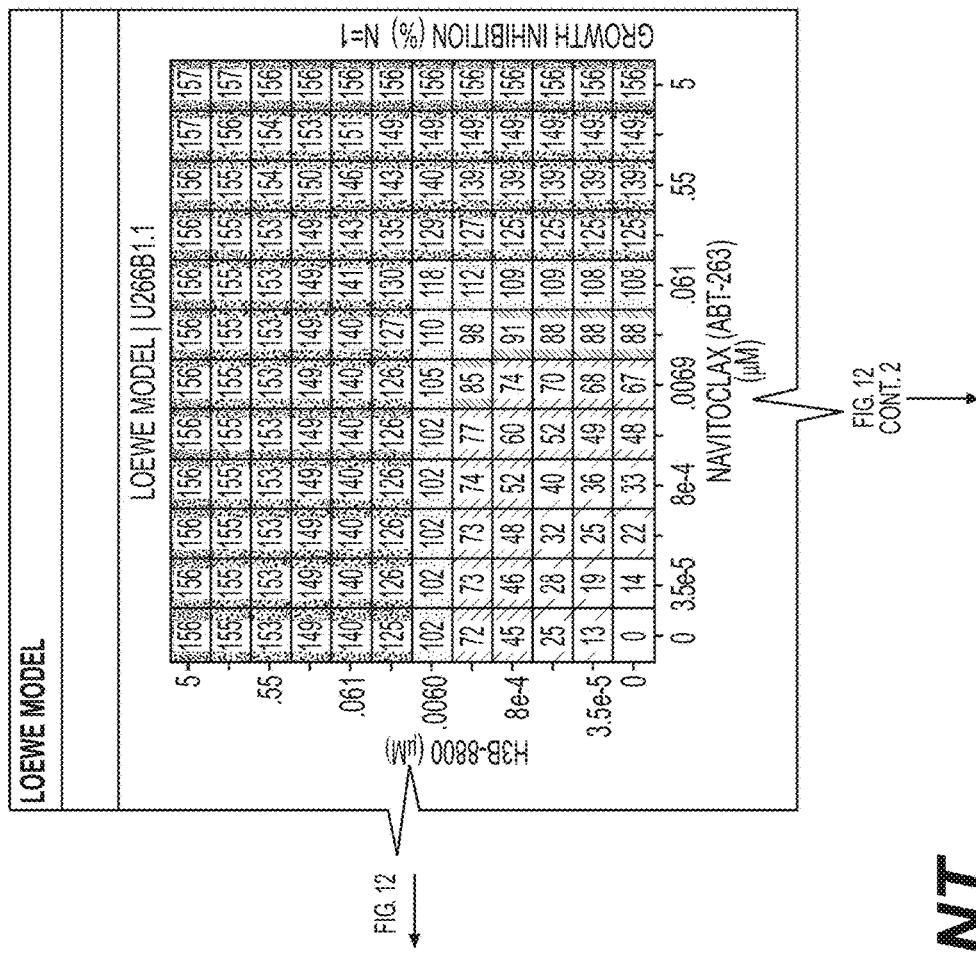
Figure 12:
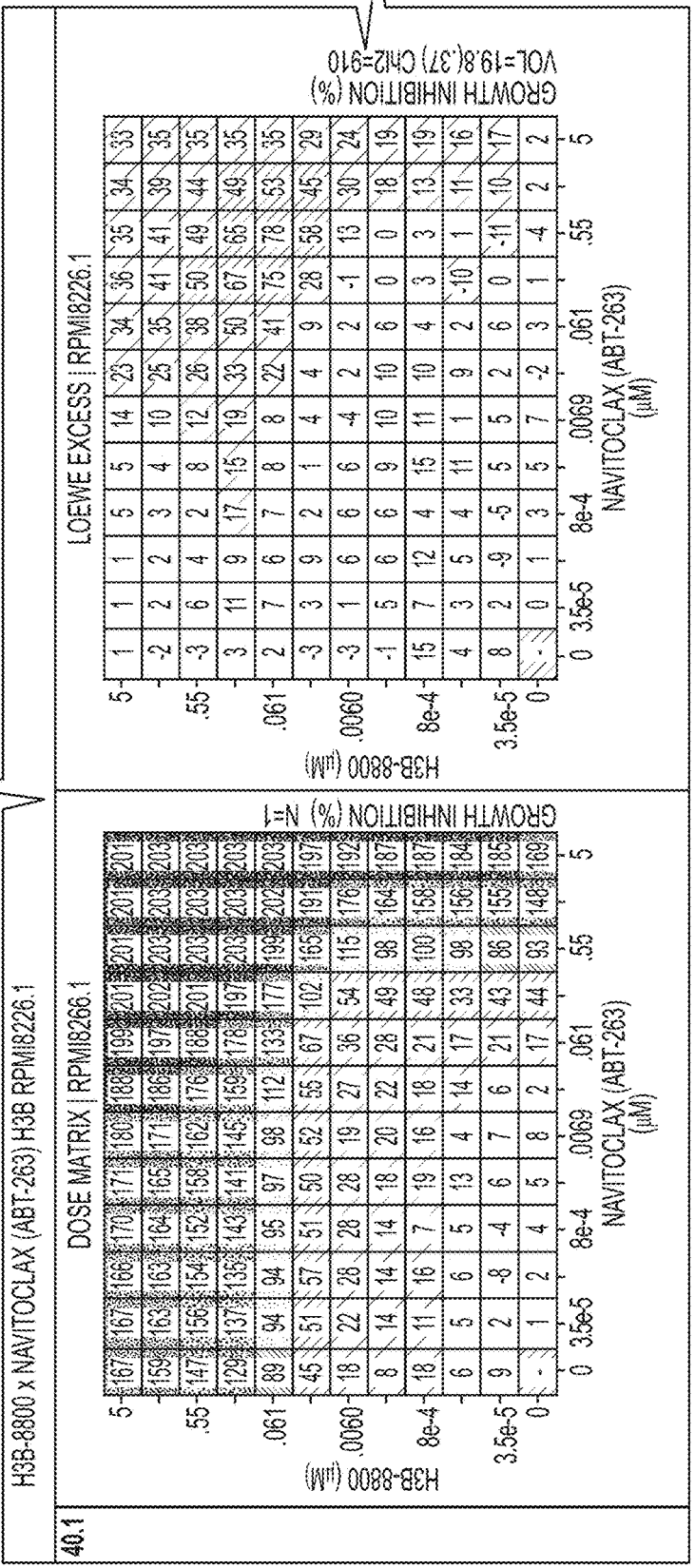
Figure 12:
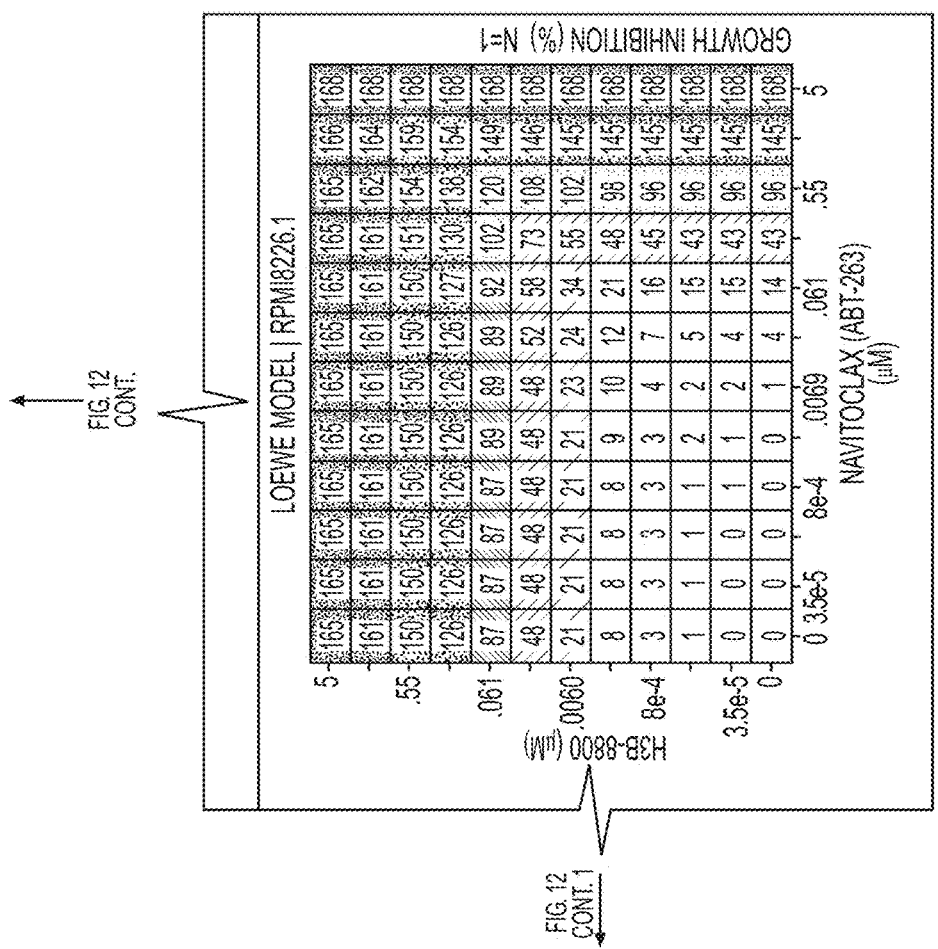

ABT263 (Navitoclax), a BCL2/BCLxL/BCLw pan inhibitor, was tested in combination with H3B-8800 in an 12×12 dose matrix mode. Combination of the two inhibitors showed strong synergistic effect with large excess over the Loewe additivity model (FIG. 12) in two different multiple myeloma cell line models including U266B1 (synergy score=41.3), and RPM18226 (synergy score=40.1).

Figure 13:
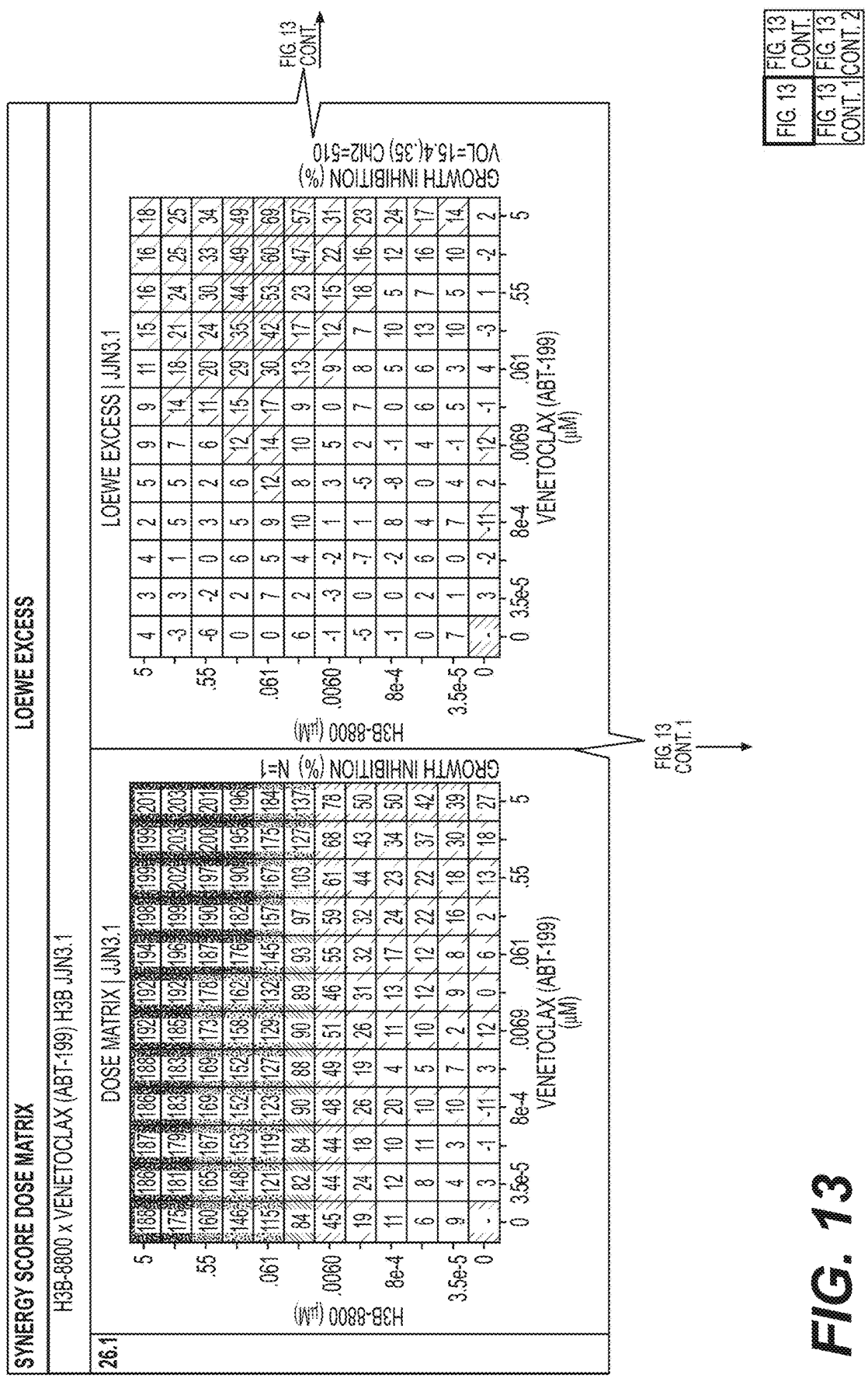
FIG. 13 shows the synergistic effect of treatment with H3B-8800 and ABT199 in two multiple myeloma cell lines: JJN3 and RPM18226.
Figure 13:
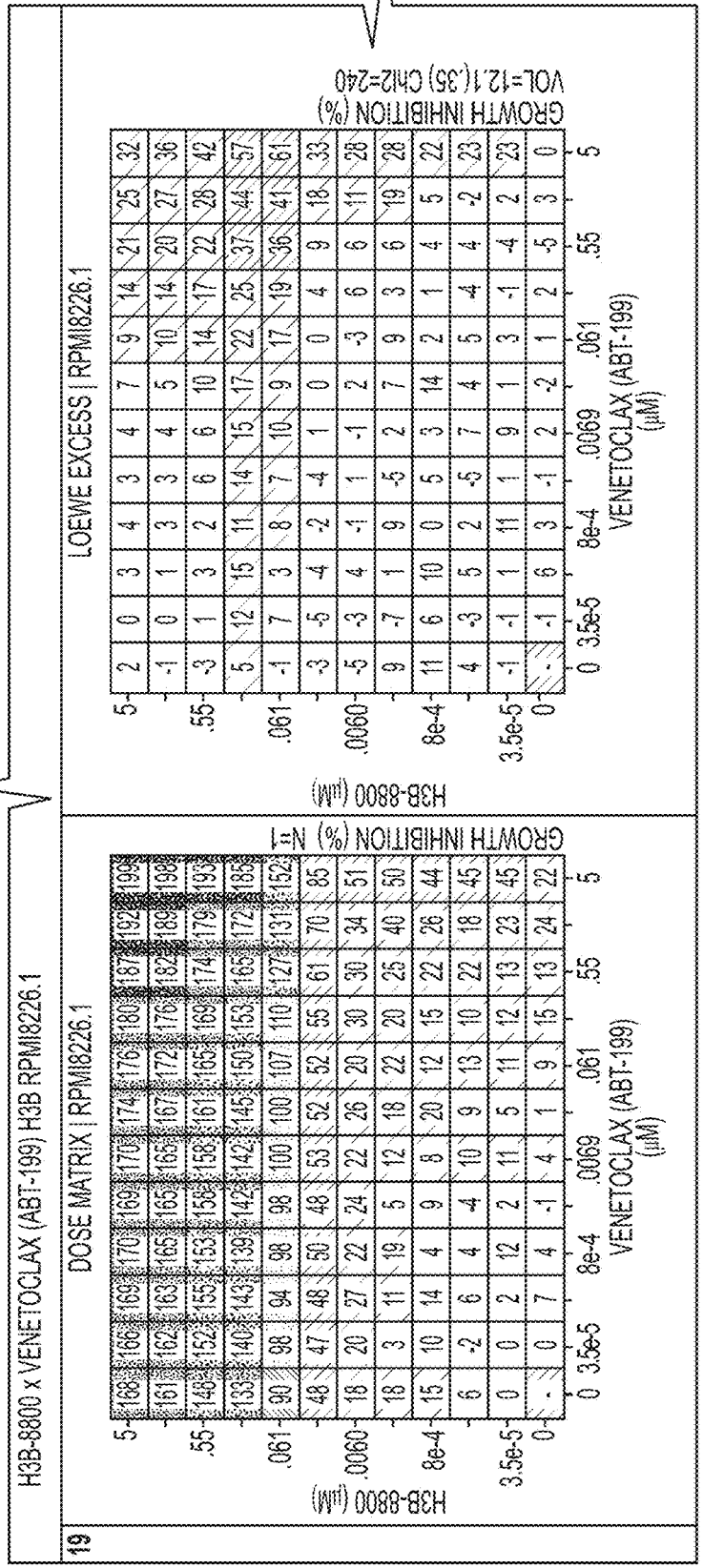
Figure 13:
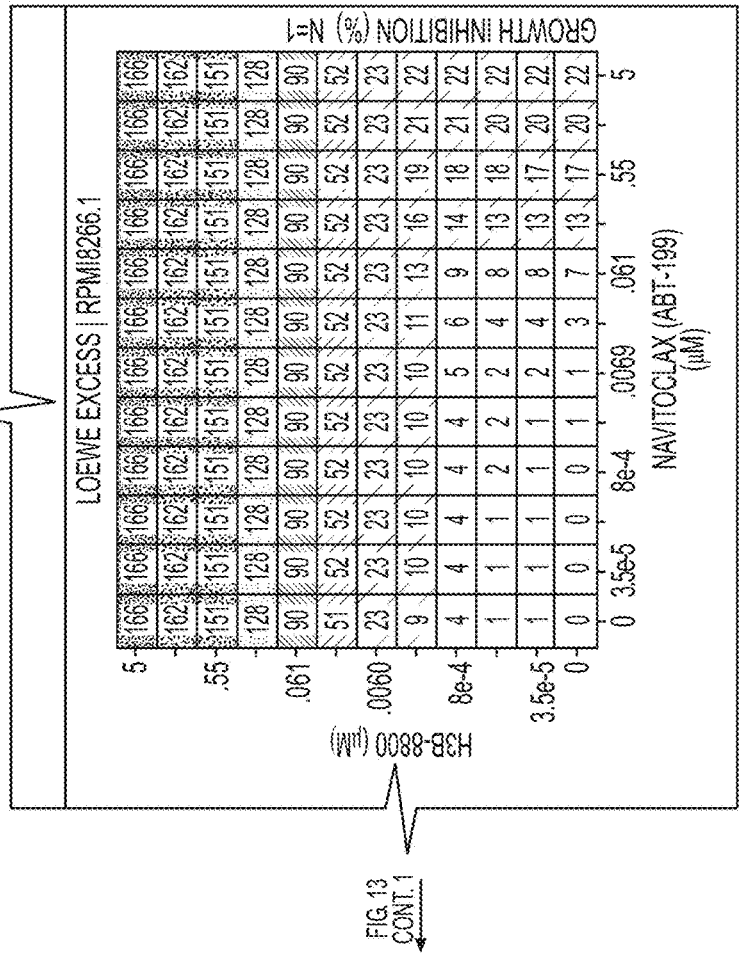

ABT199 (venetoclax) was also tested in combination with H3B-8800. ABT199 is a more BCL2-selective inhibitor that is active on BCLxL. Combination of H3B-8800 and ABT199 also demonstrated a synergistic activity in two tested multiple myeloma cell line models JJN3 (synergy score=26.1), and RPM18226 (synergy score=19) (FIG. 13).

Figure 14:
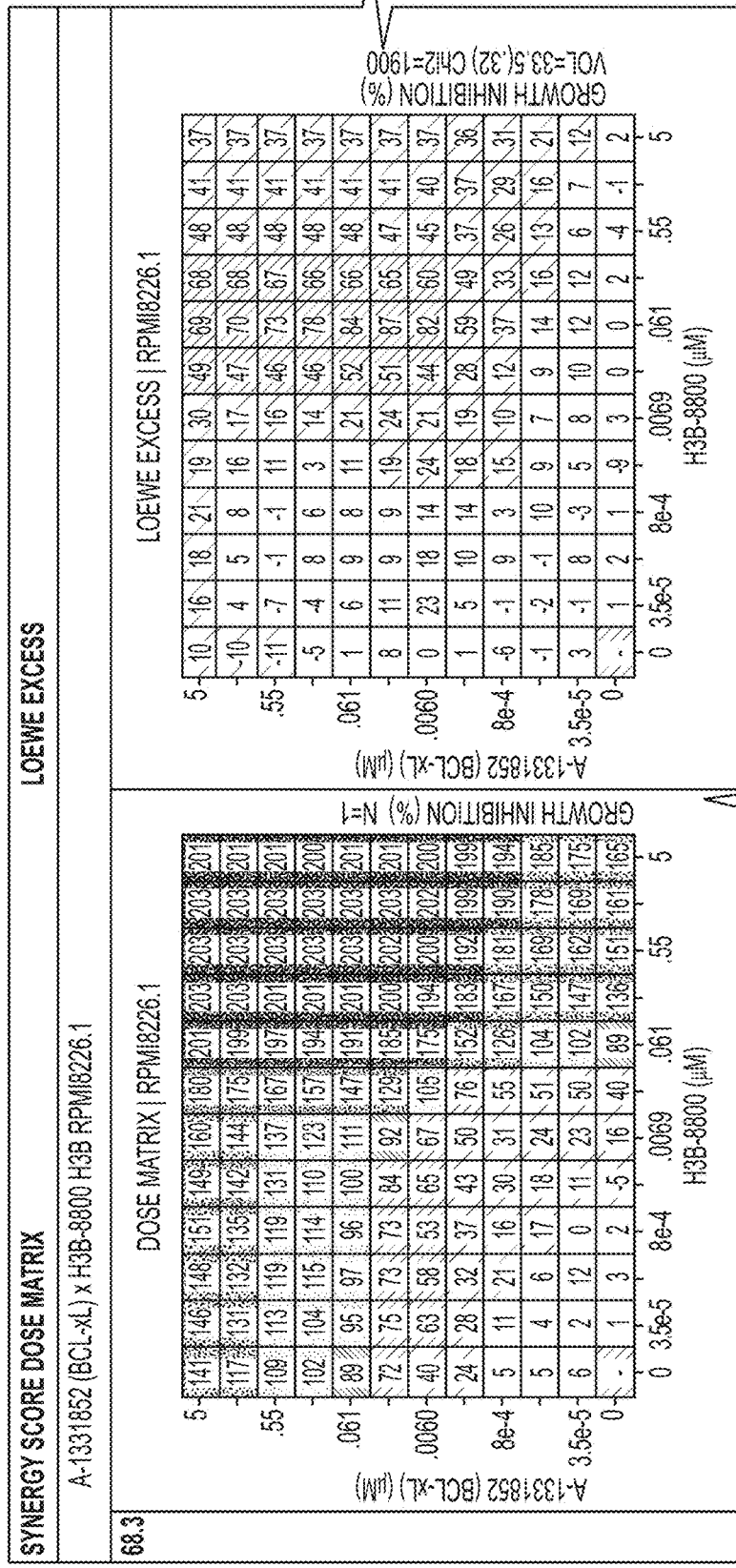
FIG. 14 shows the synergistic effect of treatment with H3B-8800 and A-1331852 in two multiple myeloma cell lines: RPM18226 and MM1S.
Figure 14:
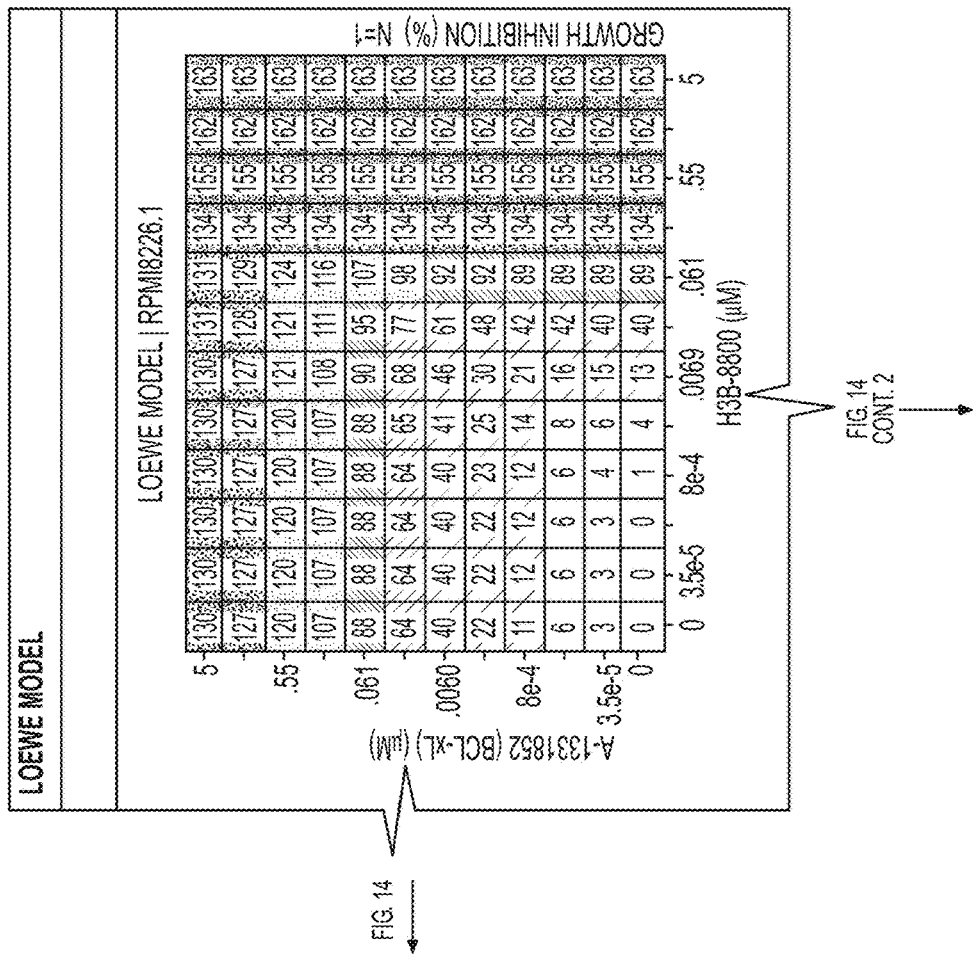
Figure 14:
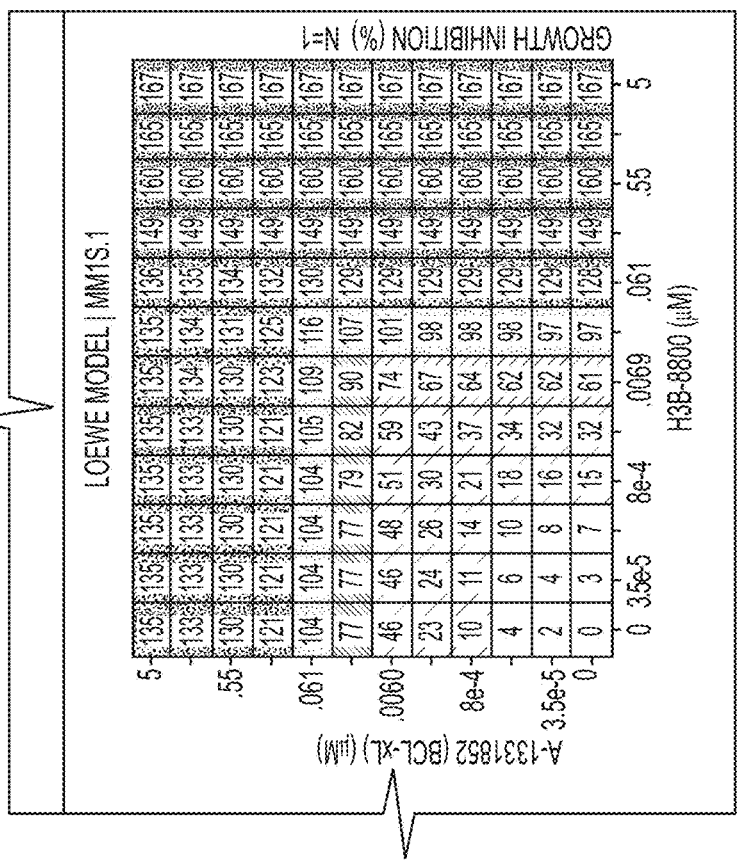

In addition, A-1331852 was also tested in combination with H3B-8800. A-1331852 is a more BCLxL-selective inhibitor. Combination of H3B-880 and A-1331852 demonstrated a substantial synergistic activity in two tested multiple myeloma cell line models RPM18226 (synergy score=68.3), and MM1S (synergy score=56.8) (FIG. 14).

Taken together, these data indicate that combination of pladienolide-derived splicing modulators (e.g., E7107 or H3B-8800) with BCL2, BCL2/BCLxL, or BCLxL inhibitors (e.g., ABT263, ABT199 or A-1331852) induces synergistic cytotoxicity in a variety of cancer cells. This data therefore supports using the combination of pladienolide splicing modulators and BCL2, BCL2/BCLxL, or BCLxL inhibitors in the treatment of cancer.

---

The invention claimed is:

1. A method of treating cancer comprising administering to a subject in need thereof
   (i) a therapeutically effective amount of at least one spliceosome modulator chosen from E7107, H3B-8800, and pharmaceutically acceptable salts thereof, and
   (ii) a therapeutically effective amount of at least one inhibitor chosen from BCL2 inhibitors, BCL2/BCLxL inhibitors, and BCLxL inhibitors, wherein the at least one spliceosome modulator is administered simultaneously, separately, or sequentially with the at least one inhibitor.

2. The method of claim 1, wherein the at least one spliceosome modulator is chosen from E7107 and pharmaceutically acceptable salts thereof.

3. The method of claim 1, wherein the at least one spliceosome modulator is chosen from H3B-8800 and pharmaceutically acceptable salts thereof.

4. The method of claim 1, wherein the at least one spliceosome modulator is stereoisomerically pure.

5. The method of claim 1, wherein the at least one spliceosome modulator comprises greater than about 80% by weight of one stereoisomer.

6. The method of claim 1, wherein the at least one spliceosome modulator comprises greater than about 90% by weight of one stereoisomer.

7. The method of claim 1, wherein the at least one spliceosome modulator comprises greater than about 95% by weight of one stereoisomer.

8. The method of claim 1, wherein the at least one spliceosome modulator comprises greater than about 97% by weight of one stereoisomer.

9. The method of claim 1, wherein the at least one inhibitor is chosen from HA14-1, BH3I-1, antimycin A, chelerythrine, gossypol (NSC19048), apogossypol (NSC736630), TW-37, 4-(3-methoxy-phenylsulfonyl)-7-nitro-benzofuran-3-oxide (MNB), TM12-06, obatoclax (GX15-070), venetoclax (ABT199), navitoclax (ABT263), A-1331852, ABT737, and pharmaceutically acceptable salts thereof.

10. The method of claim 1, wherein the at least one inhibitor is chosen from venetoclax (ABT199), navitoclax (ABT263), A-1331852, ABT737, and pharmaceutically acceptable salts thereof.

11. The method of claim 1, wherein the at least one inhibitor is venetoclax (ABT199) or a pharmaceutically acceptable salt thereof.

12. The method of claim 1, wherein the at least one inhibitor is chosen from navitoclax (ABT263) and pharmaceutically acceptable salts thereof.

13. The method of claim 1, wherein the at least one inhibitor is chosen from ABT737 and pharmaceutically acceptable salts thereof.

14. The method of claim 1, wherein the at least one inhibitor is chosen from A-1331852 and pharmaceutically acceptable salts thereof.

15. The method of claim 1, wherein the at least one spliceosome modulator is formulated for intravenous, oral, subcutaneous, or intramuscular administration.

16. The method of claim 1, wherein the at least one spliceosome modulator is formulated for oral administration.

17. The method of claim 1, wherein the at least one inhibitor is formulated for intravenous, oral, subcutaneous, or intramuscular administration.

18. The method of claim 1, wherein the at least one inhibitor is formulated for oral administration.

19. The method of claim 1, wherein the at least one spliceosome modulator and the at least one inhibitor are administered sequentially.

20. The method of claim 1, wherein the at least one spliceosome modulator and the at least one inhibitor are administered separately.

21. The method of claim 1, wherein the at least one spliceosome modulator and the at least one inhibitor are administered simultaneously.

22. The method of claim 1, wherein said cancer is chosen from myelodysplastic syndrome, multiple myeloma, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

23. The method of claim 1, wherein said cancer is lung cancer.

24. The method of claim 1, wherein said cancer is selected from non-small cell lung carcinoma and small cell lung carcinoma.

25. The method of claim 1, wherein said cancer is a hematological cancer.

26. The method of claim 25, wherein said hematological cancer is chosen from Hodgkin's lymphoma, non-Hodgkin's lymphoma, myelodysplastic syndrome, multiple myeloma, chronic lymphocytic leukemia, acute lymphoblastic leukemia, acute myelogenous leukemia, chronic myelogenous leukemia, chronic myelomonocytic leukemia, and acute myeloid leukemia.

27. The method of claim 1, wherein said cancer is a solid tumor.

28. The method of claim 27, wherein said solid tumor is chosen from colon or colorectal cancer, pancreatic cancer, endometrial cancer, ovarian cancer, breast cancer, melanoma, gastric cancer, cholangiocarcinoma, prostate cancer, cervical cancer, glioma, and lung cancer.

29. The method of claim 28, wherein said melanoma is uveal melanoma.

30. The method of claim 1, wherein said cancer is a MCL1-dependent cancer.

31. The method of claim 30, wherein said MCL1-dependent cancer is selected from acute lymphoblastic leukemia, acute myelogenous leukemia, chronic lymphocytic leukemia, chronic myelogenous leukemia, chronic myelomonocytic leukemia, acute monocytic leukemia, Hodgkin's lymphoma, non-Hodgkin's lymphoma, myelodysplastic syndrome, multiple myeloma, lung cancer, breast cancer, pancreatic cancer, prostate cancer, colon or colorectal cancer, gastric cancer, cervical cancer, endometrial cancer, ovarian cancer, cholangiocarcinoma, glioma, and melanoma.

32. The method of claim 1, wherein said cancer is positive for one or more mutations in a spliceosome gene or protein.

33. The method of claim 32, wherein said spliceosome gene or protein is chosen from splicing factor 3B subunit 1 (SF3B1), U2 small nuclear RNA auxiliary factor 1 (U2AF1), serine/arginine-rich splicing factor 2 (SRSF2), zinc finger (CCCH type) RNA-binding motif and serine/arginine rich 2 (ZRSR2), pre-mRNA-processing-splicing factor 8 (PRPF8), U2 small nuclear RNA auxiliary factor 2 (U2AF2), splicing factor 1 (SF1), splicing factor 3a subunit 1 (SF3A1), PRP40 pre-mRNA processing factor 40 homolog B (PRPF40B), RNA binding motif protein 10 (RBM10), poly(rC) binding protein 1 (PCBP1), crooked neck pre-mRNA splicing factor 1 (CRNKL1), DEAH (Asp-Glu-Ala-His) box helicase 9 (DHX9), peptidyl-prolyl cis-trans isomerase-like 2 (PPIL2), RNA binding motif protein 22 (RBM22), small nuclear ribonucleoprotein Sm D3 (SNRPD3), probable ATP-dependent RNA helicase DDX5 (DDX5), pre-m RNA-splicing factor ATP-dependent RNA helicase DHX15 (DHX15), and polyadenylate-binding protein 1 (PABPC1).

34. The method of claim 33, wherein said spliceosome gene or protein is splicing factor 3B subunit 1 (SF3B1).

* * * * *

UNITED STATES PATENT AND TRADEMARK OFFICE
CERTIFICATE OF CORRECTION

| | |
|---|---|
| PATENT NO. | : 11,524,009 B2 |
| APPLICATION NO. | : 16/760313 |
| DATED | : December 13, 2022 |
| INVENTOR(S) | : Daniel Aird et al. |

It is certified that error appears in the above-identified patent and that said Letters Patent is hereby corrected as shown below:

In the Claims

Claim 33, Column 22, Line 56, "pre-m RNA-splicing" should read as --pre-mRNA-splicing--.

Signed and Sealed this
Eleventh Day of April, 2023

Katherine Kelly Vidal
*Director of the United States Patent and Trademark Office*

SEQUENCE LISTING

```
<160> NUMBER OF SEQ ID NOS: 12

<210> SEQ ID NO 1
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      DEAH box helicase 9 (DHX9) peptide"

<400> SEQUENCE: 1

Asp Glu Ala His
1

<210> SEQ ID NO 2
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
```

-continued

```
atatgccaaa ccagctccta c                                        21

<210> SEQ ID NO 3
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
aaggacaaaa cgggactgg                                           19

<210> SEQ ID NO 4
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 4
agaactccac aaacccatcc cagc                                     24

<210> SEQ ID NO 5
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
aaagccaatg ggcaggt                                             17

<210> SEQ ID NO 6
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
ccaccttcta ggtcctctac at                                       22

<210> SEQ ID NO 7
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 7
tccacaaacc catcttggaa ggcc                                     24

<210> SEQ ID NO 8
<211> LENGTH: 20
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic primer"

<400> SEQUENCE: 8
gacaaaggag gccgtgagga                                                     20

<210> SEQ ID NO 9
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
gtttgttacg ccgtcgctga aa                                                  22

<210> SEQ ID NO 10
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 10
tcaggcatgc ttcggaaact gga                                                 23

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
gctcactctt cagtcggaaa t                                                   21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
gcatcgaacc attagcagaa a                                                   21
```